(12) United States Patent
Löscher et al.

(10) Patent No.: US 11,273,174 B2
(45) Date of Patent: Mar. 15, 2022

(54) IODINE COMPOSITIONS

(71) Applicant: NOVALIQ GMBH, Heidelberg (DE)

(72) Inventors: Frank Löscher, Schriesheim (DE); Ralf Grillenberger, Ilvesheim (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 16/606,936

(22) PCT Filed: Apr. 20, 2018

(86) PCT No.: PCT/EP2018/060197
§ 371 (c)(1),
(2) Date: Oct. 21, 2019

(87) PCT Pub. No.: WO2018/193093
PCT Pub. Date: Oct. 25, 2018

(65) Prior Publication Data
US 2020/0129543 A1 Apr. 30, 2020

(30) Foreign Application Priority Data
Apr. 21, 2017 (EP) .................................... 17167561

(51) Int. Cl.
| | |
|---|---|
| *A61K 33/18* | (2006.01) |
| *A61K 9/00* | (2006.01) |
| *A61K 47/06* | (2006.01) |
| *A61K 8/20* | (2006.01) |
| *A61K 8/70* | (2006.01) |
| *A61K 9/06* | (2006.01) |
| *A61K 9/08* | (2006.01) |
| *A61K 47/10* | (2017.01) |
| *A61K 9/14* | (2006.01) |
| *A61P 17/02* | (2006.01) |
| *A61P 27/02* | (2006.01) |
| *A61P 31/02* | (2006.01) |
| *A61Q 17/00* | (2006.01) |

(52) U.S. Cl.
CPC ............... *A61K 33/18* (2013.01); *A61K 8/20* (2013.01); *A61K 8/70* (2013.01); *A61K 9/0014* (2013.01); *A61K 9/0048* (2013.01); *A61K 9/06* (2013.01); *A61K 9/08* (2013.01); *A61K 9/145* (2013.01); *A61K 47/06* (2013.01); *A61K 47/10* (2013.01); *A61P 17/02* (2018.01); *A61P 27/02* (2018.01); *A61P 31/02* (2018.01); *A61Q 17/005* (2013.01)

(58) Field of Classification Search
CPC .... A61K 33/18; A61K 9/0014; A61K 9/0048; A61K 47/06; A61K 8/20; A61K 8/70; A61K 9/06; A61K 9/08; A61K 47/10; A61K 9/145; A61K 45/06; A61P 17/02; A61P 27/02; A61P 31/02; A61Q 17/005
See application file for complete search history.

(56) References Cited

U.S. PATENT DOCUMENTS

| | | | |
|---|---|---|---|
| 2,616,927 A | 11/1952 | Kauck et al. | |
| 4,452,818 A | 6/1984 | Haidt | |
| 5,077,036 A | 12/1991 | Long | |
| 5,126,127 A | 6/1992 | Bhagwat et al. | |
| 5,326,566 A | 7/1994 | Parab | |
| 5,336,175 A | 8/1994 | Mames | |
| 5,518,731 A | 5/1996 | Meadows | |
| 5,667,809 A | 9/1997 | Trevino et al. | |
| 5,874,469 A | 2/1999 | Maniar et al. | |
| 5,874,481 A | 2/1999 | Weers et al. | |
| 5,980,936 A | 11/1999 | Krafft et al. | |
| 5,981,607 A | 11/1999 | Ding et al. | |
| 6,042,845 A | 3/2000 | Sun et al. | |
| 6,060,085 A | 5/2000 | Osborne | |
| 6,113,919 A | 9/2000 | Reiss et al. | |
| 6,159,977 A | 12/2000 | Reeves | |
| 6,177,477 B1 | 1/2001 | George et al. | |
| 6,197,323 B1 | 3/2001 | Georgieff | |
| 6,224,887 B1 | 5/2001 | Samour et al. | |
| 6,262,126 B1 | 7/2001 | Meinert | |
| 6,294,563 B1 | 9/2001 | Garst | |
| 6,335,335 B2 | 1/2002 | Higashiyama | |
| 6,372,243 B2 | 4/2002 | Kobuch | |
| 6,391,879 B1 | 5/2002 | Reeves | |
| 6,458,376 B1 | 10/2002 | Meadows | |
| 6,486,212 B2 | 11/2002 | Meinert | |
| 6,489,367 B1 | 12/2002 | Meinert | |
| 6,730,328 B2 | 5/2004 | Maskiewicz et al. | |
| 7,001,607 B1 | 2/2006 | Menz et al. | |
| 7,026,359 B1 | 4/2006 | Gross et al. | |
| 7,258,869 B1 | 8/2007 | Berry et al. | |
| 7,740,875 B2 | 6/2010 | Dechow | |
| 8,029,977 B2 | 10/2011 | Meinert et al. | |
| 8,222,292 B2 | 7/2012 | Goskonda et al. | |
| 8,470,873 B2 | 6/2013 | Chen | |
| 8,614,178 B2 | 12/2013 | Theisinger et al. | |
| 8,796,340 B2 | 8/2014 | Theisinger et al. | |
| 8,916,157 B2 | 12/2014 | Krause et al. | |
| 8,986,738 B2 | 3/2015 | Meinert | |
| 9,241,900 B2 | 1/2016 | Wilson | |
| 9,308,262 B2 | 4/2016 | Günther et al. | |
| 9,757,459 B2 | 9/2017 | Günther et al. | |

(Continued)

FOREIGN PATENT DOCUMENTS

| | | |
|---|---|---|
| CN | 1147213 A | 4/1997 |
| CN | 200977281 | 11/2007 |

(Continued)

OTHER PUBLICATIONS

"Does Iodine Dissolve in Ethanol?"—an internet article obtained from the webpage https://www.enotes.com/homework-help/do-iodine-dissolve-ethanol-557516 (dated Nov. 19, 2015) (Year: 2015).*

(Continued)

*Primary Examiner* — Sin J Lee
(74) *Attorney, Agent, or Firm* — Hoxie & Associates LLC

(57) ABSTRACT

The present invention relates to compositions comprising molecular iodine and a vehicle comprising a semifluorinated alkane. The compositions of the invention may be used to treat or prevent diseases or conditions caused by, or associated with microorganisms.

23 Claims, No Drawings

(56) References Cited

U.S. PATENT DOCUMENTS

| | | | |
|---|---|---|---|
| 9,757,460 | B2 | 9/2017 | Günther et al. |
| 9,770,508 | B2 | 9/2017 | Günther et al. |
| 10,045,996 | B2 | 8/2018 | Theisinger et al. |
| 2002/0004063 | A1 | 1/2002 | Zhang |
| 2002/0064565 | A1* | 5/2002 | Karagoezian ......... A61P 29/00 424/661 |
| 2002/0128527 | A1 | 9/2002 | Meinert |
| 2003/0018044 | A1 | 1/2003 | Peyman |
| 2003/0027833 | A1 | 2/2003 | Cleary et al. |
| 2003/0170194 | A1 | 9/2003 | Piotrowiak |
| 2004/0101551 | A1 | 5/2004 | Selzer |
| 2004/0265362 | A1 | 12/2004 | Susilo |
| 2004/0266702 | A1 | 12/2004 | Dawson et al. |
| 2005/0079210 | A1 | 4/2005 | Gupta |
| 2005/0084553 | A1* | 4/2005 | Moon .................. A61K 8/9767 424/773 |
| 2005/0175541 | A1 | 8/2005 | Lanza et al. |
| 2005/0274744 | A1 | 12/2005 | Spada et al. |
| 2005/0288196 | A1 | 12/2005 | Horn |
| 2006/0153905 | A1 | 7/2006 | Carrara et al. |
| 2008/0050335 | A1 | 2/2008 | Faour et al. |
| 2008/0153909 | A1 | 6/2008 | Dana et al. |
| 2008/0207537 | A1 | 8/2008 | Turner et al. |
| 2008/0234389 | A1 | 9/2008 | Mecozzi et al. |
| 2008/0260656 | A1 | 10/2008 | Mallard |
| 2009/0169601 | A1 | 7/2009 | Koch et al. |
| 2010/0006600 | A1 | 1/2010 | Dascanio |
| 2010/0008996 | A1 | 1/2010 | Meinert |
| 2010/0016814 | A1 | 1/2010 | Gokhale et al. |
| 2010/0137252 | A1* | 6/2010 | Matsumura ............ A61K 36/61 514/78 |
| 2010/0226997 | A1 | 9/2010 | Bowman et al. |
| 2010/0274215 | A1 | 10/2010 | Wong et al. |
| 2011/0269704 | A1 | 11/2011 | Seigfried |
| 2012/0010280 | A1 | 1/2012 | Aleo et al. |
| 2012/0095097 | A1 | 4/2012 | Tabuchi et al. |
| 2012/0100183 | A1 | 4/2012 | Schlessinger et al. |
| 2012/0219640 | A1* | 8/2012 | Wright ................ A61K 9/0014 424/667 |
| 2012/0238639 | A1 | 9/2012 | Theisinger et al. |
| 2012/0244177 | A1 | 9/2012 | Theisinger et al. |
| 2013/0011484 | A1 | 1/2013 | Bevier |
| 2013/0046014 | A1 | 2/2013 | Theisinger et al. |
| 2013/0084250 | A1 | 4/2013 | Hagedorn et al. |
| 2013/0266652 | A1 | 10/2013 | Theisinger et al. |
| 2013/0303473 | A1 | 11/2013 | Wilson |
| 2013/0336557 | A1 | 12/2013 | Cruzat et al. |
| 2014/0004197 | A1 | 1/2014 | Theisinger et al. |
| 2014/0100180 | A1 | 4/2014 | Gunther et al. |
| 2014/0140942 | A1 | 5/2014 | Gunther et al. |
| 2014/0303219 | A1* | 10/2014 | Bingaman .............. A61P 43/00 514/372 |
| 2014/0369993 | A1 | 12/2014 | Gunther et al. |
| 2015/0045282 | A1 | 2/2015 | Elsohly et al. |
| 2015/0224064 | A1 | 8/2015 | Gunther et al. |
| 2015/0238605 | A1 | 8/2015 | Gunther et al. |
| 2016/0101178 | A1 | 4/2016 | Wilson |
| 2016/0159902 | A1 | 6/2016 | Günther et al. |
| 2016/0243189 | A1 | 8/2016 | Gu et al. |
| 2017/0020726 | A1 | 1/2017 | Labombarbe et al. |
| 2017/0044096 | A1* | 2/2017 | Laskin .................. A61K 47/55 |
| 2017/0087100 | A1 | 3/2017 | Scherer et al. |
| 2017/0087101 | A1 | 3/2017 | Scherer et al. |
| 2017/0182060 | A1 | 6/2017 | Wiedersberg et al. |
| 2018/0360908 | A1 | 12/2018 | Beier et al. |
| 2019/0274970 | A1 | 9/2019 | Günther et al. |
| 2019/0321218 | A1 | 10/2019 | Graf et al. |
| 2019/0328717 | A1 | 10/2019 | Günther et al. |
| 2019/0343793 | A1 | 11/2019 | Günther et al. |
| 2020/0129543 | A1 | 4/2020 | Loscher et al. |

FOREIGN PATENT DOCUMENTS

| | | |
|---|---|---|
| CN | 202136470 U | 2/2012 |
| CN | 203524843 U | 4/2014 |
| EP | 0593552 | 4/1994 |
| EP | 0 670 159 | 9/1995 |
| EP | 0 965 329 | 12/1999 |
| EP | 0 965 334 | 12/1999 |
| EP | 0 939 655 | 6/2002 |
| EP | 1 152 749 | 4/2006 |
| EP | 2 110 126 | 10/2009 |
| EP | 2 332 525 | 6/2011 |
| EP | 2 335 735 | 6/2011 |
| EP | 2 462 921 | 6/2012 |
| JP | S5721312 A | 2/1982 |
| JP | S6452722 | 2/1989 |
| JP | H0764702 B2 | 7/1995 |
| JP | 2000511157 | 8/2000 |
| JP | 2001/58734 | 6/2001 |
| JP | 2008/505177 | 2/2008 |
| JP | 2011/006348 | 1/2011 |
| JP | 2011/024841 A | 2/2011 |
| WO | WO 1995/033447 | 12/1995 |
| WO | WO 96/40052 | 12/1996 |
| WO | WO 97/12852 | 4/1997 |
| WO | WO 1998/42313 | 10/1998 |
| WO | WO 1998/005301 | 12/1998 |
| WO | WO 00/10531 | 3/2000 |
| WO | WO 00/24376 | 5/2000 |
| WO | WO 00/54588 | 9/2000 |
| WO | WO 2002/049631 | 6/2002 |
| WO | WO 2003/061389 | 7/2003 |
| WO | WO 2005/018530 | 3/2005 |
| WO | WO 2005/099718 | 10/2005 |
| WO | WO 2005/099752 | 10/2005 |
| WO | WO 2005/123035 | 12/2005 |
| WO | WO 2006/007510 | 1/2006 |
| WO | WO 2006/042059 | 4/2006 |
| WO | WO 2006/048242 | 5/2006 |
| WO | WO 2007/052288 | 5/2007 |
| WO | WO 2008/019146 | 2/2008 |
| WO | WO 2008/060359 | 5/2008 |
| WO | WO 2009/013435 | 1/2009 |
| WO | WO 2009/065565 | 5/2009 |
| WO | WO 2010/062394 | 6/2010 |
| WO | WO 2010/146536 | 12/2010 |
| WO | WO 2011/009436 | 1/2011 |
| WO | WO 2011/073134 | 6/2011 |
| WO | WO 2011/113855 | 9/2011 |
| WO | WO 2012/007776 | 1/2012 |
| WO | WO 2012/052418 | 4/2012 |
| WO | WO 2012/062834 | 5/2012 |
| WO | WO 2012/093113 | 7/2012 |
| WO | WO 2012/121754 | 9/2012 |
| WO | WO 2012/160179 | 11/2012 |
| WO | WO 2012/160180 | 11/2012 |
| WO | WO 2013/110621 | 8/2013 |
| WO | WO 2014/041055 | 3/2014 |
| WO | WO 2014/041071 | 3/2014 |
| WO | WO 2014/154531 | 10/2014 |
| WO | WO 2015/011199 | 1/2015 |
| WO | WO 2015/053829 | 4/2015 |
| WO | WO 2015/074137 | 5/2015 |
| WO | WO 2016/025560 | 2/2016 |
| WO | WO 2016/109531 | 7/2016 |
| WO | WO 2017/220625 | 12/2017 |
| WO | WO 2018/054932 | 3/2018 |
| WO | WO 2018/055101 | 3/2018 |
| WO | WO 2018/060282 | 4/2018 |
| WO | WO 2018/114557 | 6/2018 |
| WO | WO 2018/115097 | 6/2018 |

OTHER PUBLICATIONS

Bardin et al., "Long-Range Nanometer-Scale Organization of Semifluorinated Alkane Monolayers at the Air/Water Interface," Langmuir, 2011, 27, 13497-13505.

(56) References Cited

OTHER PUBLICATIONS

Broniatowski, M. et al., "Langmuir Monolayers Characteristic of (Perfluorodecyl)-Alkanes," Journal of Physical Chemistry B, 2004, 108, 13403-13411.
Costa Gomes et al., "Solubility of dioxygen in seven fluorinated liquids," Journal of Fluorine Chemistry, 2004, 125, 1325-1329.
Dembinski, R. et al., "Semi-fluorinated Alkanes as Carriers for Drug Targeting in Acute Respiratory Failure," Experimental Lung Research, 2010, 36, 499-507.
Dias et al., "Solubility of oxygen in liquid perfluorocarbon," Fluid Phase Equilibria, 2004, 222-223:325-330.
Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).
English-language machine translation of EP0670159 (A1) issued in U.S. Appl. No. 14/122,025 dated Apr. 1, 2015, 10 pages.
Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Hardung, H., "Semifluorierte und perfluorierte Vethindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).
Hardung, H., "Semifluorierte und perfluorierte Vethindungen zur topischen und parenteralen Anwendung," 2008, English Language Abstract, 2 pages, retrieved from https://freidok.uni-freiburg.de/data/5682 (retrieved on Jul. 10, 2017).
Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.
Holm, R. et al., "A novel excipient, 1-perfluorohexyloctane shows limited utility for the oral delivery of poorly water-soluble drugs," European Journal of Pharmaceutical Sciences, 2011, 42: 416-422.
International Preliminary Report on Patentability dated Sep. 18, 2012, for International Patent Application PCT/EP2011/053949, 9 Pages.
International Preliminary Report on Patentability for International Application No. PCT/EP2011/068141 dated Apr. 23, 2013, 4 pages.
International Preliminary Report on Patentability for International Application No. PCT/EP2011/069795 dated May 14, 2013, 8 pages.
International Preliminary Report on Patentability for International Application No. PCT/EP2012/050043 dated Jul. 10, 2013, 5 pages.
International Preliminary Report on Patentability for International Application No. PCT/EP2012/059787 dated Nov. 26, 2013, 9 pages.
International Preliminary Report on Patentability for International Application No. PCT/EP2012/059788 dated Nov. 26, 2013, 8 pages.
International Preliminary Report on Patentability for International Application No. PCT/EP2013/051163 dated Jul. 29, 2014, 7 pages.
International Preliminary Report on Patentability for International Application No. PCT/EP2013/068882 dated Mar. 17, 2015, 5 pages.
International Preliminary Report on Patentability for International Application No. PCT/EP2013/068909 dated Mar. 17, 2015, 7 pages.
International Preliminary Report on Patentability dated Jan. 26, 2016, for International Application No. PCT/EP2014/065840, 11 pages.
International Preliminary Report on Patentability dated Dec. 25, 2018, for International Application No. PCT/EP2017/065163, 6 pages.
International Preliminary Report on Patentability dated Mar. 26, 2019, for International Application No. PCT/EP2017/073697, 7 pages.
International Preliminary Report on Patentability dated Mar. 26, 2019, for International Application No. PCT/EP2017/074079, 7 pages.
International Preliminary Report on Patentability dated Apr. 2, 2019, for International Application No. PCT/EP2017/074545, 7 pages.
International Preliminary Report on Patentability dated Jun. 25, 2019, for International Application No. PCT/EP2017/082739, 7 pages.
International Preliminary Report on Patentability dated Oct. 22, 2019, for International Application No. PCT/EP2018/060197, 6 pages.
International Search Report for International Application No. PCT/EP2011/053949 dated Sep. 6, 2011, 5 pages.
International Search Report for International Application No. PCT/EP2011/068141 dated Dec. 14, 2011, 2 pages.
International Search Report for International Application No. PCT/EP2011/069795 dated Jan. 16, 2012, 3 pages.
International Search Report for International Application No. PCT/EP2012/050043 dated Apr. 24, 2012, 2 pages.
International Search Report for International Application No. PCT/EP2012/059787 dated Dec. 5, 2012, 4 pages.
International Search Report for International Application No. PCT/EP2012/059788 dated Dec. 3, 2012, 4 pages.
International Search Report for International Application No. PCT/EP2013/051163 dated Mar. 4, 2013, 4 pages.
International Search Report for International Application No. PCT/EP2013/068882 dated Oct. 30, 2013, 4 pages.
International Search Report for International Application No. PCT/EP2013/068909 dated Dec. 5, 2013, 4 pages.
International Search Report for International Application No. PCT/EP2014/065840 dated Oct. 7, 2014, 4 pages.
International Search Report for International Application No. PCT/EP2016/073262 dated Nov. 18, 2016, 5 pages.
International Search Report for International Application No. PCT/EP2016/073263 dated Dec. 23, 2016, 3 pages.
International Search Report for International Application No. PCT/EP2017/065163, dated Aug. 8, 2017, 3 pages.
International Search Report for International Application No. PCT/EP2017/073697 dated Nov. 6, 2017, 4 pages.
International Search Report for International Application No. PCT/EP2017/074079 dated Dec. 22, 2017, 4 pages.
International Search Report for International Application No. PCT/EP2017/074545 dated Nov. 28, 2017, 3 pages.
International Search Report for International Application No. PCT/EP2017/082739 dated Mar. 6, 2018, 3 pages.
International Search Report for International Application No. PCT/EP2017/083770 (revised version) dated Jul. 6, 2018, 4 pages.
International Search Report and Written Opinion for International Application No. PCT/EP2017/083770 dated Jul. 6, 2018, 14 pages.
International Search Report for International Application No. PCT/EP2018/060197 dated Jul. 9, 2018, 4 pages.
JP 2000511157 A, English Machine Translation of the Abstract, Description, and Claims, Espacenet, Date Accessed: Feb. 10, 2016, 15 pages.
JPS6452722, English Machine Translation of the Abstract, Description, and Claims, Espacenet, Date Accessed: Feb. 10, 2016, 4 pages.
Kociok, N., et al, "Influence on Membrane-Mediated Cell Activation by Vesicles of Silicone Oil or Perfluorohexyloctane," Graefe's Archive for Clinical and Experimental Ophthalmology, 2005, 243, 345-358.
Meinert, H. et al., "The Use of Semifluorinated Alkanes in Blood-Substitutes," Biomaterials, Artificial Cells, and Immobilization Biotechnology, 1993, 21 (5), 583-595.
Meinert, H. et al., "Semifluorinated Alkanes—A New Class of Compounds with Outstanding Properties for Use in Ophthalmology," European Journal of Ophthalmology, 2000, 10 (3), 189-197.
Messmer, et al. "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.

(56) References Cited

OTHER PUBLICATIONS

Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016. Poster No. PSa03-02, English Translation of Abstract, p. 138.

O'Rourke, M. et al., "Enhancing Delivery of Topical Ocular Drops," Cataract & Refractive Surgery Today Europe, 2016, 2 pages.

Plassmann, M. et al., "Trace Analytical Methods for Semifluorinated n-Alkanes in Snow, Soil, and Air," Analytical Chemistry, 2010, 82(11), 4551-4557.

Plassmann, M. et al., "Theoretical and Experimental Simulation of the Fate of Semifluorinated n-Alkanes During Snowmelt," Environmental Science & Technology, 2010, 44 (17), 6692-6697.

Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.

Steven, P. et al. "Semifluorinated Alkane Eye Drops for Treatment of Dry Eye Disease—A Prospective, Multicenter Noninterventional Study" Journal of Ocular Pharmacology and Therapeutics (2015) vol. 31(8):498-503.

Steven, P. et al. "Semifluorinated Alkane Eye Drops for Treatment of Dry Eye Disease—A Prospective, Multicenter Noninterventional Study," Investigative Ophthalmology & Visual Science, 2015, 56:4493, Abstract Only (1 page).

Steven et al., "Semifluorinated Alkane Eye Drops for Treatment of Dry Eye Disease Due to Meibomian Gland Disease," Journal of Ocular Pharmacology and Therapeutics, 2017, 33(9):1-8.

Wong, D. et al., "Perfluorocarbon and Semifluorinated Alkanes," Seminars in Ophthalmology, 2000, 15 (1), 25-35.

Zhang et al., "Surface micelles of semifluorinated alkanes in Langmuir-Blodgett monolayers," Phys. Chem. Chem. Phys., 2004, 6, 1566-1569.

Bertilla et al., "Semifluorinated Alkanes as Stabilizing Agents of Fluorocarbon Emulsions," Springer, Tokyo, 2005, International Symposia for Life Sciences and Medicine, vol. 12, pp. 237-251.

Davies, "Biopharmaceutical Considerations in Topical Ocular Drug Delivery," Clin. Exper. Pharmacol. Physiol., 2000, 27:558-562.

Deschamps, J. et al., "Solubility of oxygen, carbon dioxide and water in semifluorinated alkanes and in perfluorooctylbromide by molecular simulation", Journal of Fluorine Chemistry, Elsevier, vol. 125, No. 3, 2004.

Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).

German, E.J., et al., "Reality of drop size from multi-dose eye drop bottles: is it cause for concern?" Eye, 1999, 13:93-100.

Griffin, W., "Classification of Surface-Active Agnets by 'HLB'," Journal of The Society of Cosmetic Chemists,1949, 1:311-326.

JPH0764702B2, Kanebo LTD, "Cosmetic of Polyphasic Emulsion Type," Jul. 12, 1995, English language machine translation of abstract, Espacenet, date obtained: Apr. 30, 2021, 1 page <https://worldwide.espacenet.com/patent/search/family/014142733/publication/JPH0764702B2?q=JPH0764702B2>.

JPS5721312A, Green Cross Corp, "Breathable Ointment," Apr. 2, 1982, English language machine translation of abstract, Espacenet, date obtained: Apr. 30, 2021, 1 page <https://worldwide.espacenet.com/patent/search/family/014132731/publication/JPS5721312A?q=JPS5721312A>.

Kaercher et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.

Matteucci et al., "Biocompatibility assessment of liquid artificial vitreous replacements: relevance of in vitro studies," Survey of Ophthalmology, 2007, 52(3):289-299, Abstract Only (1 page).

Yaoxue Zhuanye Zhishi II (Editor: Jin Xiangqun), Military Medical Science Press, $1^{st}$ Printing of $2^{nd}$ Edition, Mar. 2009, p. 158.

Yaoxue Zhuanye Zhishi II (Editor: Jin Xiangqun), Military Medical Science Press, $1^{st}$ Printing of $2^{nd}$ Edition, Mar. 2009, p. 158, 3 pages (English Machine Translation).

* cited by examiner

IODINE COMPOSITIONS

CROSS-REFERENCE TO RELATED APPLICATIONS

This application is a U.S. national stage application filed under 35 U.S.C. § 371 of International Application No. PCT/EP2018/060197, filed on Apr. 20, 2018, which claims priority to, and the benefit of, European Application No. 17167561.4, filed Apr. 21, 2017, the contents of each of which are incorporated herein by reference in their entireties.

BACKGROUND OF THE INVENTION

Iodine compositions are useful as topical antiseptics and disinfectants. Tinctures of iodine are compositions based on a hydroalcoholic solution of elemental iodine, iodide salt in ethanol and water which have long been used for such purposes. Such tinctures are however highly irritating and toxic, and are thus not suitable for administration, for example, to sensitive tissues such as the eye. Many iodine compositions in the art are based alternatively on povidone iodine, also known PVP-iodine or polyvinylpyrrolidone-iodine, as a source and reservoir of free molecular iodine, and to improve the solubility of iodine in the aqueous environment.

Examples of ophthalmic compositions comprising povidone-iodine are described for example in EP0526695A1 and WO2011084473A1. Such compositions rely on extensive formulation, requiring the addition of pH buffers or adjusting agents, stabilizing agents, and other excipients to provide stability and adequate shelf-life.

Iodine compositions based on non-aqueous medium, such as organic solvents have also previously been disclosed. For example, US 2012/0219640 discloses iodine compositions for use in treating topical skin conditions such as athelete's foot infection, comprising organic solvents such as ethanol, iso-propyl alcohol and acetone. Such solvents are not universably applicable in terms of therapeutic use due to tissue toxicity or poor biocompatibility. WO 2012/007776 A2 proposes the use of a siloxane vehicle, to prepare disinfectant and antiseptic solutions of iodine. Siloxanes however may tend to be viscous and for topical applications, may feel greasy and have limited spreadability. They also tend to have refractive indexes which are differentiated from that of human tear fluid and thus may not be suitable or patient-friendly for ophthalmic applications.

It is an object of the present invention, to provide iodine compositions which may avoid some of the disadvantages of the prior art, and which may be useful as an antiseptic or a disinfectant, such as in the treatment or prophylaxis of diseases and conditions caused or associated with microorganisms. Further objects of the invention will be clear on the basis of the following description of the invention, examples and claims.

SUMMARY OF THE INVENTION

In a first aspect, the invention relates to a composition comprising molecular iodine and a vehicle comprising a semifluorinated alkane. In some embodiments, the vehicle comprises a semifluorinated alkane is of formula (II): $CF_3(CF_2)_n$—$(CH_2)_mCH_3$ wherein n and m are each independently selected from an integer from 3 to 10. In another aspect, the composition may be essentially free of water.

In a further aspect, the invention provides for a composition comprising molecular iodine and a vehicle comprising a semifluorinated alkane, for use as a medicament, preferably for the treatment or prevention of a disease or condition of the skin or mucosal tissue; or the eye or an ophthalmic tissue; preferably wherein the disease or condition is associated with, or caused by a microorganism.

DETAILED DESCRIPTION OF THE INVENTION

The present invention relates to a composition comprising molecular iodine and a vehicle comprising a semifluorinated alkane.

Molecular iodine, which may also be referred to as elemental iodine, has a chemical formula of $I_2$, and is metallic grey/dark coloured solid with a molecular weight of 253.81 g/mol. Molecular iodine has been found to be effective in destroying or inhibiting the growth/proliferation of microorganisms such as bacteria, fungi, demodex and viruses.

The vehicle of the composition according to invention serves as a carrier for molecular iodine, and may be in the form of a liquid, semi-solid or solid. Preferably, the molecular iodine is dissolved and/or fully miscible in the vehicle i.e. the composition of the invention does not comprise of any particulate or solid phase iodine, preferably at room temperature conditions i.e. between 15 and 25° C.

In one preferred embodiment, the vehicle is a liquid. Preferably, the molecular iodine is dissolved in the liquid vehicle to form a clear solution. The term "clear solution" or "solution" as such, as understood herein, refers to a liquid solution in which all solutes are fully dissolvable or dissolved under room temperature conditions i.e. between 15 and 25° C. The resulting solution does not comprise of any particulate or solid phase components. In the present invention, the molecular iodine is preferably completely dissolved in the liquid vehicle comprising a semifluorinated alkane, which, depending on degree of dilution, may provide clear, purple to pink coloured solutions.

The composition according to invention comprises a semifluorinated alkane (which may also be referred to in abbreviated form as an SFA), which may be defined as a linear or branched compound composed of at least one perfluorinated segment (F-segment) and at least one non-fluorinated hydrocarbon segment (H-segment).

Preferably, the semifluorinated alkane is a linear compound composed of one perfluorinated segment (F-segment) and one non-fluorinated hydrocarbon segment (H-segment). In a branched semifluorinated alkane, the semifluorinated alkane may comprise of a branched non-fluorinated hydrocarbon segment, wherein the hydrocarbon segment comprises as a substituent, one or more of an alkyl group selected from the group consisting of —$CH_3$, —$C_2H_5$, —$C_3H_7$ and —$C_4H_9$.

In particular, the present invention relates to composition comprising molecular iodine and a vehicle comprising a semifluorinated alkane, wherein the semifluorinated alkane is of formula $$CF_3(CF_2)_n\text{—}R_m \qquad \text{Formula (I)}$$

wherein n is an integer selected from 1 to 12, and R is linear or branched alkyl or cycloalkyl with m carbon atoms, wherein m is an integer selected from 2 to 12.

In one preferred embodiment, said vehicle may comprise of a semifluorinated alkane of Formula (I), wherein n is an integer selected from 3 to 10, and R is linear or branched alkyl or cycloalkyl with m carbon atoms, wherein m is an integer selected from 4 to 8.

In the above embodiments, where R is preferably a branched alkyl, R may be selected from iso-propyl, any one of the butyl isomers, such as iso-butyl, sec-butyl, or tert-butyl, any one of the pentyl isomers such as neo-pentyl, tert-pentyl, sec-pentyl, iso-pentyl, or 3-pentyl; any one of the hexyl or heptyl isomers, and any one of the octyl isomers, for example such as iso-octyl.

In another preferred embodiment, said vehicle may comprise of a semifluorinated alkane of Formula (I), wherein n is an integer selected from 3 to 10, and R is linear alkyl with m carbon atoms, wherein m is an integer selected from 4 to 8.

In an alternative preferred embodiment, said vehicle may comprise of a semifluorinated alkane of Formula (I), wherein n is an integer selected from 3 to 10, and R is linear alkyl with m carbon atoms, wherein m is an integer selected from 2 to 8.

As understood herein, the term linear alkyl may refer to unbranched and straight-chain alkyl groups. For example, R of Formula (I) may preferably be selected from ethyl, n-propyl, n-butyl, n-pentyl, n-hexyl, or n-heptyl, and n-octyl.

In another preferred embodiment, said vehicle may comprise of a semifluorinated alkane of Formula (I), wherein n is an integer selected from 3 to 10, and R is cycloalkyl with m carbon atoms, wherein m is an integer selected from 4 to 8.

As understood herein, the term cycloalkyls may refer to cyclic, i.e. ring-forming alkyl groups, such as cyclobutyl, cyclopentyl or cyclohexyl.

In a preferred embodiment, the semifluorinated alkane featured in the compositions according to the invention is a liquid, i.e. a compound that exists in a liquid state at least at one temperature within the temperature range of 4° C. to 50° C. Preferably, the semifluorinated alkane featured in the composition according to the invention is a compound that is a liquid at room temperature (RT), such as between the temperature of 15° C. to 25° C. Alternatively, the semifluorinated alkane, or optionally, a mixture of two or more semifluorinated alkanes, featured in the composition may be semi-solid or solid at room temperature but has a melting point of at least one temperature within the range from 26° C. to 45° C.

In another particularly preferred embodiment, the present invention relates to a composition comprising molecular iodine and a vehicle comprising a semifluorinated alkane of formula (II):

wherein n and m are each independently selected from an integer from 3 to 10.

Preferably, said semifluorinated alkane may be selected from $CF_3(CF_2)_3$—$(CH_2)_4CH_3$ (F4H5), $CF_3(CF_2)_3$—$(CH_2)_5CH_3$ (F4H6), $CF_3(CF_2)_5$—$(CH_2)_5CH_3$ (F6H6), $CF_3(CF_2)_5$—$(CH_2)_7CH_3$ (F6H8), $CF_3(CF_2)_3$—$(CH_2)_7CH_3$ (F4H8), $CF_3(CF_2)_7$—$(CH_2)_7CH_3$ (F8H8) and $CF_3(CF_2)_9$—$(CH_2)_4CH_3$ (F10H5). More preferably, said semifluorinated alkane may be selected from $CF_3(CF_2)_3$—$(CH_2)_4CH_3$ (F4H5) and $CF_3(CF_2)_5$—$(CH_2)_7CH_3$ (F6H8). In another embodiment, the composition may comprise of molecular iodine dissolved in any one of said selected semifluorinated alkanes.

In another alternative embodiment, the present invention relates to a composition comprising molecular iodine and a vehicle comprising a semifluorinated alkane of formula (II):

wherein n is an integer selected from 2 to 9 and m is an integer from 1 to 7.

Said semifluorinated alkane may be selected from $CF_3(CF_2)_3$—$(CH_2)_4CH_3$ (F4H5), $CF_3(CF_2)_3$—$(CH_2)_5CH_3$ (F4H6), $CF_3(CF_2)_5$—$CH_2CH_3$ (F6H2), $CF_3(CF_2)_5$—$(CH_2)_5CH_3$ (F6H6), $CF_3(CF_2)_5$—$(CH_2)_7CH_3$ (F6H8), $CF_3(CF_2)_3$—$(CH_2)_7CH_3$ (F4H8), $CF_3(CF_2)_7$—$(CH_2)_7CH_3$ (F8H8) and $CF_3(CF_2)_9$—$(CH_2)_4CH_3$ (F10H5). More preferably, said semifluorinated alkane may be selected from $CF_3(CF_2)_5$—$CH_2CH_3$ (F6H2), $CF_3(CF_2)_3$—$(CH_2)_4CH_3$ (F4H5) and $CF_3(CF_2)_5$—$(CH_2)_7CH_3$ (F6H8). In another embodiment, the composition may comprise of molecular iodine dissolved in any one of said selected semifluorinated alkanes.

In another particularly preferred embodiment, the present invention relates to a composition comprising molecular iodine and a vehicle comprising a semifluorinated alkane of formula (II):

wherein n and m are each independently selected from an integer from 3 to 10, and wherein the composition is essentially free of water. In such embodiment, preferably, the semifluorinated alkane may be selected from $CF_3(CF_2)_3$—$(CH_2)_4CH_3$ (F4H5), $CF_3(CF_2)_3$—$(CH_2)_5CH_3$ (F4H6), $CF_3(CF_2)_5$—$(CH_2)_5CH_3$ (F6H6), $CF_3(CF_2)_5$—$(CH_2)_7CH_3$ (F6H8), $CF_3(CF_2)_3$—$(CH_2)_7CH_3$(F4H8), $CF_3(CF_2)_7$—$(CH_2)_7CH_3$ (F8H8) and $CF_3(CF_2)_9$—$(CH_2)_4CH_3$ (F10H5).

In yet a further embodiment, the present invention relates to a composition comprising molecular iodine and a vehicle comprising a semifluorinated alkane of formula (II):

wherein n is an integer selected from 2 to 9 and m is an integer from 1 to 7, and wherein the composition is essentially free of water. In such embodiment, preferably, the semifluorinated alkane may be selected from $CF_3(CF_2)_3$—$(CH_2)_4CH_3$ (F4H5), $CF_3(CF_2)_3$—$(CH_2)_5CH_3$ (F4H6), $CF_3(CF_2)_5$—$CH_2CH_3$ (F6H2), $CF_3(CF_2)_5$—$(CH_2)_5CH_3$ (F6H6), $CF_3(CF_2)_5$—$(CH_2)_7CH_3$ (F6H8), $CF_3(CF_2)_3$—$(CH_2)_7CH_3$(F4H8), $CF_3(CF_2)_7$—$(CH_2)_7CH_3$ (F8H8) and $CF_3(CF_2)_9$—$(CH_2)_4CH_3$ (F10H5).

The alternative nomenclature for the specified semifluorinated alkanes as noted in parentheses above and as may be further used herein, is based on the general formula FnHm, wherein F means the linear perfluorinated hydrocarbon segment, H means the linear non-fluorinated hydrocarbon segment and n, m is the number of carbon atoms of the respective segment. For example, F4H5 may be used to denote 1-perfluorobutyl pentane or $CF_3(CF_2)_3$—$(CH_3)_4CH_3$ (which may be also, alternatively expressed as formula $F(CF_2)_4(CH_2)_5H$), which has a linear perfluorinated segment F with four carbons (n=4) and a linear non-fluorinated hydrocarbon segment with 5 carbons (m=5).

Most preferably, the compositions of the invention comprise of molecular iodine and a liquid vehicle comprising, or consisting of a semifluorinated alkane selected from $F(CF_2)_6(CH_2)_2H$ (F6H2), $F(CF_2)_4(CH_2)_5H$ (F4H5) and $F(CF_2)_6(CH_2)_8H$ (F6H8). The particular preferred semifluorinated alkane, F6H2, also known as perfluorohexyl-ethane, and which has the chemical formula $F(CF_2)_6(CH_2)_2H$ is a chemically and physiologically inert, water-insoluble liquid, with a density of 1.57 g/cm3 at 20° C. and refractive index of 1.295 at 20° C. The particular preferred semifluorinated alkane, F4H5, also known as 1-perfluorobutyl-pentane, and which has the chemical formula $F(CF_2)_4(CH_2)_5H$ is a chemically and physiologically inert, water-insoluble liquid, with a density of 1.284 g/cm³ at 25° C. and refractive index of 1.3204 at 20° C. The particularly preferred semifluorinated alkane, F6H8, comprised by the liquid vehicle of the composition of the present invention also known as 1-perfluorohexyl-octane, is also a chemically and physiologically inert, water-insoluble liquid, and has a density of 1.35 g/cm³ at 25° C. and refractive index of 1.3432 at 20° C. In a preferred embodiment, said compositions may be substantially free of water.

The vehicle of the compositions of the invention comprising of "a" semifluorinated alkane is to be understood herein, as comprising of at least one semifluorinated alkane, preferably of Formula (I) or (II) or any of the other formulas as described above. Optionally, however, the vehicle of the composition may comprise of more than one, for example, a mixture of two or more semifluorinated alkanes of Formula (I) or (II) or any one of the semifluorinated alkane species as described above.

In yet further embodiment, the vehicle of the composition may consist of a semifluorinated alkane of Formula (I) or (II) or any one of the semifluorinated alkanes as specified above. In this context, the term 'a' semifluorinated alkane is to be understood as at least one semifluorinated alkane, but may also include the option of more than one, or a plurality of semifluorinated alkane compounds. Accordingly, in one embodiment, the vehicle of the composition may consist of more than one semifluorinated alkane of Formula (I) or (II) or any one of the semifluorinated alkanes as specified above. Preferably, said semifluorinated alkane (or optionally, mixture of two or more semifluorinated alkanes) is present and functionally featured in the composition as a vehicle for the molecular iodine. In an optional embodiment, said compositions may however include a further active ingredient and/or one or more excipients. In an embodiment of the invention, the composition may have a vehicle consisting of a semifluorinated alkane or a mixture of semifluorinated alkanes as defined and optionally, one or more excipients, or a co-solvent.

In a preferred embodiment, the composition of the present invention may consist of molecular iodine, and optionally a further active ingredient, and a vehicle comprising a semifluorinated alkane. In a further preferred embodiment, the composition may consist of molecular iodine, and optionally a further active ingredient, and a vehicle consisting of one or more semifluorinated alkanes and optionally one or more non-polar co-solvents or excipients. Optionally, the composition may consist of molecular iodine and a vehicle consisting of one or more semifluorinated alkanes. Optionally, the composition may consist of molecular iodine and a vehicle consisting of a semifluorinated alkane.

In one embodiment, the invention relates to a composition consisting of a) molecular iodine and optionally, a further active ingredient, and b) a vehicle consisting of a semifluorinated alkane and optionally a non-polar co-solvent or excipient; wherein the semifluorinated alkane is of formula (I) $CF_3(CF_2)_n-R_m$ wherein n is an integer selected from 1 to 12, and R is linear or branched alkyl or cycloalkyl with m carbon atoms, wherein m is an integer selected from 2 to 12.

In another embodiment, the invention relates to a composition consisting of a) molecular iodine and optionally, a further active ingredient, and b) a vehicle consisting of a semifluorinated alkane and optionally a non-polar co-solvent or excipient; wherein the semifluorinated alkane is of formula (I) $CF_3(CF_2)_n-R_m$ wherein n is an integer selected from 2 to 12, and R is linear or branched alkyl or cycloalkyl with m carbon atoms, wherein m is an integer selected from 2 to 12.

As used herein, the term "consists" and related terms "consisting" or "consist" is to be understood as meaning that no other features, other than those prefaced by the term are present. In the context of compositions, if any other constituent or component is present in the composition other than those prefaced by such term, then it is present only in trace or residual amounts such as to confer no technical advantage or relevance in respect of the object of the invention, such as may be further understood by the term 'essentially" or "substantially" used in conjunction with these terms (e.g. 'essentially consisting of"). In contrast, the term 'comprising" or related terms "comprises" or "comprise" in the context of compositions, is to be understood as meaning that other features, other than those prefaced by the term may be present in the composition.

In an alternative aspect of the invention, the compositions of the invention may comprise of molecular iodine ($I_2$) and a vehicle comprising a perfluorocarbon. As understood herein, a perfluorocarbon is a hydrocarbon compound wherein all hydrogen atoms are replaced by another atom, namely predominantly or entirely by fluorine atoms. Preferably, the perfluorocarbon or perfluorinated hydrocarbon has 5 to 12 carbon atoms. Preferably, the perfluorocarbon is a liquid at room temperature. In another embodiment, the perfluorocarbon may be compound of formula $F(CF_2)_nF$, wherein n is an integer selected from 5 to 12. Particularly preferred perfluorocarbons are perfluorooctane, and perfluorodecalin. Optionally, said compositions may comprise also a semifluorinated alkane, preferably of Formula (I) or (II) as described above.

Preferably, the amount of iodine incorporated in the composition according to the invention, when used in a therapeutic or prophylactic application, is present in an amount effective to inhibit or prevent growth and/or proliferation of a microorganism. In another aspect, the molecular iodine may preferably be incorporated in the composition in an amount that is useful for producing a desired pharmacological effect, such as a pharmacological effect in the treatment of any one of the conditions or diseases as will be further described in detail below.

In one aspect, a composition of the invention such as described in any of the above embodiments, comprises an amount of molecular iodine of less than 1 mg/mL, or preferably less than 0.9 mg/mL, 0.8 mg/mL, 0.6 mg/mL, 0.5 mg/mL, 0.4 mg/mL, 0.2 mg/mL, 0.1 mg/mL, 0.05 mg/mL, 0.01 mg/mL or less than 0.001 mg/mL.

In one embodiment, the composition of the invention may comprise of less than 1 mg/mL of molecular iodine dissolved in the vehicle.

In another embodiment, the composition of the invention may comprise or consist of an amount of molecular iodine of between 0.001 mg/mL and 1 mg/mL, or between 0.001 mg/mL and any one of the values of 0.9 mg/mL, 0.8 mg/mL, 0.6 mg/mL, 0.5 mg/mL, 0.4 mg/mL, 0.2 mg/mL, 0.1 mg/mL, 0.05 mg/mL, 0.01 mg/mL, dissolved in the vehicle, preferably a vehicle consisting of a semifluorinated alkane as defined in any one of the above embodiments, and optionally a compatible e.g. non-polar, co-solvent or an excipient.

In one embodiment, the composition may comprise less than 1 mg/mL, or preferably less than 0.9 mg/mL, 0.8 mg/mL, 0.6 mg/mL, 0.5 mg/mL, 0.4 mg/mL, 0.2 mg/mL, 0.1 mg/mL, 0.05 mg/mL, 0.01 mg/mL or less than 0.001 mg/mL of molecular iodine dissolved in the vehicle. In an embodiment where the vehicle may consist of only a semifluorinated alkane, the composition may comprise less than 1 mg/mL, or less than 0.9 mg/mL, 0.8 mg/mL, 0.6 mg/mL, 0.5 mg/mL, 0.4 mg/mL, 0.2 mg/mL, 0.1 mg/mL, 0.05 mg/mL, 0.01 mg/mL or less than 0.001 mg/mL of molecular iodine dissolved in said semifluorinated alkane vehicle.

In another embodiment where the vehicle may consist of only a semifluorinated alkane and optionally a non-polar and/or aprotic solvent, or an excipient, the composition may comprise less than 1 mg/mL, or less than 0.9 mg/mL, 0.8 mg/mL, 0.6 mg/mL, 0.5 mg/mL, 0.4 mg/mL, 0.2 mg/mL, 0.1 mg/mL, 0.05 mg/mL, 0.01 mg/mL or less than 0.001 mg/mL of molecular iodine dissolved in said vehicle comprising of a semifluorinated alkane and optional co-solvent(s). Preferably, such compositions are non-staining and/or stable for at least 30, 90 or 180 days at room temperature.

According to an aspect of the invention, the composition may comprise of molecular iodine and a vehicle comprising of a semifluorinated alkane, such as described in any of the above embodiments, wherein the vehicle also further comprises a co-solvent.

As understood herein, a co-solvent is a compound which is suitable for enhancing solubility or solubilizing molecular iodine and/or any other solid or non-miscible component featured in the composition of the invention. Said solid or non-miscible component may be, for example a further active ingredient, or another excipient. Preferably, the co-solvent component of the composition is a liquid that is fully miscible with the semifluorinated alkane, i.e. it mixes with the semifluorinated alkane to form a coherent and single phase, to serve as a vehicle and carrier for molecular iodine and/or any other component, such as a further active ingredient or a further excipient. The co-solvent preferably is a liquid organic compound which is physiologically tolerated and safe for direct topical administration to the eye, eye tissue and/or to skin, dermal, or mucosal tissue.

Preferably, the co-solvent is a non-polar solvent. The non-polar solvent may be non-ionizable, and/or aprotic, preferably such co-solvent does not support the formation of an iodine ion or oxidized iodine species, preferably the co-solvent is a solvent that does not support the formation as of any one (or combination of) the following: iodide (I—), triiodide (I3-), iodate (IO3-), or hypoiodate (IO—).

Particularly preferred as a co-solvent is a non-polar solvent selected from any one or mixture of a saturated hydrocarbon, preferably a C1-C10 alkane (such as n-pentane, n-hexane, n-heptane, or n-octane); mineral oil; paraffin; siloxane; and a perfluorocarbon. In further embodiment, the non-polar solvent may also be selected from saturated, unbranched or branched hydrocarbons with longer carbon chains such as C10 to C30, or C10 to C40.

In a particular preferred embodiment, the co-solvent is a solvent that does not support the formation of an iodine ion or oxidized iodine species, preferably the co-solvent is a solvent that does not support the formation of any one (or combination of) the following: iodide (I—), triiodide (I3-), iodate (IO3-), or hypoiodate (IO—).

The co-solvent may be featured in a composition according to the invention in an amount of no more than about 38 wt % based on the total weight of the vehicle. In a further embodiment, the amount of co-solvent may be in an amount of no more than 30% (w/w), 25% (w/w), 15% (w/w) or 10% (w/w), or 5% (w/w) 2% (w/w), or about 1.0% (w/w) in respect to the total amount of the vehicle.

In further embodiments, the co-solvent may be featured in an amount in the range of between 0.001 to 5% (w/w), or 0.001 to 2% (w/w), or 0.01 to 1% (w/w), or 0.1 to 1% (w/w) in respect to the total weight of the vehicle.

In an alternative aspect, the co-solvent may be selected from an alcohol. The co-solvent as an alcohol selected from any one or mixture of ethanol, methanol, propanol, or isopropanol or any alcohol that is physiologically tolerated by the eye or skin. The co-solvent may be an alcohol in absolute/anhydrous form, such as absolute ethanol, methanol, propanol, or isopropanol.

In one embodiment, the co-solvent is ethanol, and is featured in the composition in an amount of no more than 30% (w/w), 25% (w/w), 15% (w/w) or 10% (w/w), or 5% (w/w) 2% (w/w), or about 1.0% (w/w) in respect to the amount of the vehicle, optionally wherein the vehicle consists only of a semifluorinated alkane and ethanol; further optionally wherein the ethanol is absolute. Said composition may comprise an amount of at least 0.25 mg/ml, at least 0.5 mg/ml, at least 1 mg/mL, at least 1.5 mg/mL, at least 2.0 mg/mL, at least 2.5 mg/mL, at least 3.0 mg/mL or at least 5.0 mg/mL of molecular iodine dissolved in the semifluorinated alkane and ethanol vehicle.

Compositions with particularly higher concentrations of iodine may be useful, and advantageous, for example for disinfectant applications, such as for disinfecting inanimate surfaces, such as a surface of a surgical tool, instrument or means.

In one aspect of the invention, a composition according to the invention may comprise of an amount of molecular iodine of up to about 20 mg/ml. In such embodiments, a composition may comprise of an amount of molecular iodine of at least 1 mg/mL, or at least 1.5 mg/mL, or at least 2.0 mg/mL, or at least 2.5 mg/mL, at least 3.0 mg/mL, at least 5.0 mg/mL, at least 10.0 mg/mL or at least 15.0 mg/mL.

In a one embodiment, the composition may comprise an amount of up to 20 mg/mL of molecular iodine dissolved in the vehicle. The composition may comprise of an amount of molecular iodine dissolved in the vehicle of at least 1 mg/mL, or at least 1.5 mg/mL, or at least 2.0 mg/mL, or at least 2.5 mg/mL, at least 3.0 mg/mL, at least 5.0 mg/mL, at least 10.0 mg/mL or at least 15.0 mg/mL. In an embodiment where the vehicle may consist of only a semifluorinated alkane and optionally a co-solvent, the composition may comprise an amount of at least 1 mg/mL, at least 1.5 mg/mL, at least 2.0 mg/mL, at least 2.5 mg/mL, at least 3.0 mg/mL or at least 5.0 mg/mL, or at least 10.0 mg/mL or at least 15.0 mg/mL of molecular iodine dissolved in said vehicle consisting of a semifluorinated alkane and said optional co-solvent.

In yet a further embodiment of the invention relating to the composition comprising molecular iodine, and a vehicle comprising a semifluorinated alkane such as defined in any of the previous embodiments described above, the vehicle preferably comprises a semifluorinated alkane or optionally, a mixture of semifluorinated alkanes in an amount of at least 60% (w/w) with respect to the total weight of the vehicle. In other embodiments, the vehicle may comprise at least 70% (w/w), 75% (w/w), 85% (w/w), 90% (w/w), 95% (w/w), 98% or at least 99% (w/w) of a semifluorinated alkane or a mixture of semifluorinated alkanes, with respect to the total weight of the vehicle.

In one preferred embodiment, the vehicle of the composition according to the invention is 100% (w/w) of a semifluorinated alkane or mixture of semifluorinated alkanes. In another embodiment, the vehicle comprises a semifluorinated alkane or optionally, a mixture of semifluorinated alkanes in an amount of at least 60% (w/w) with respect to the total weight of the vehicle. In another embodiment, the vehicle may consist of at least 70% (w/w), 75% (w/w), 85% (w/w), 90% (w/w), 95% (w/w), 98% or at least 99% (w/w) of a semifluorinated alkane or a mixture of semifluorinated alkanes, with respect to the total weight of the vehicle, and a co-solvent or excipient, preferably a non-polar co-solvent or excipient.

The term "% (w/w)" as used herein and unless indicated refers to the amount of a component of a composition, (e.g. the composition of a vehicle) as a weight percentage in relation to the total weight of the composition (e.g. total weight of a vehicle), with 'w' denoting weight. For instance, the vehicle of a composition according to the present invention may comprise up to about 1.5% (w/w) of a co-solvent such as ethanol, relative to the total weight of the vehicle. The term "% (w/v)" likewise, unless indicated refers to the amount of a component of a composition as a weight percentage in relation to the total volume of the composition (with "w" denoting weight and "v" denoting volume).

In a further embodiment, the composition of the present invention is a rapidly evaporating formulation. Said composition is preferably antimicrobial effective (e.g. against any one or combination of bacteria, fungi, virus). Preferably, the rapidly evaporating formulation evaporates within 5 minutes, preferably within 3 minutes, more preferably within 1 minute from time of topical application to a surface, for example a tissue surface, or surface of any eye, or alternatively to an inanimate surface. Preferably, such rapidly evaporating formulation comprises molecular iodine dissolved in a vehicle comprising, or consisting of a semifluorinated alkane characterized by a boiling point of less than 140° C., even more preferably such rapidly evaporating formulation comprises molecular iodine dissolved in a vehicle comprising a semifluorinated alkane selected from the group consisting of F6H2 or F4H5. In one embodiment, such rapidly evaporating formulation comprises or consists of up to 0.5 mg/ml molecular iodine dissolved in F6H2.

In another embodiment, the compositions according to the invention may comprise further of an active ingredient dissolved in the vehicle. Preferably, the active ingredient is present in a therapeutically effective amount, which as used herein, means the active ingredient is at a dose, concentration or strength which is useful for producing the desired pharmacological effect, more specifically a pharmacological effect in the treatment of any one of the conditions or diseases as further described in detail below.

Preferably, the active ingredient is selected from the group consisting of antibiotics, anti-inflammatory agents, analgesics, anaesthetics, anti-allergic agents, and immunosupressants. The active ingredient may also be selected from a corticosteroid. Preferably the said active ingredient is suitable for co-formulation with molecular iodine.

Preferred antibiotics include fluoroquinolones (ciprofloxacin, levofloxacin, ofloxacin, moxifloxacin, gatifloxacin, and the like); aminoglycosides (tobramycin, gentamicin, neomycin, and the like); polymyxin B combinations (polymyxin B/trimethoprim, Polysporin polymyxin B/bacitracin, Neosporin polymyxin B/neomycin/gramicidin, and the like) and other antibiotics (azithromycin, ilotycin, erythromycin, bacitracin, and the like).

Preferred anti-inflammatories include corticosteroids (such as dexamethasone, prednisolone, loteprednol, difluprednate, fluorometalone, rimexolone, medrysone, hydrocortisone) or NSAIDs (such as bromfenac, nepafenac, diclofenac, flurbiprofen, suprofen, celecoxib, naproxen, rofecoxib).

Preferred anesthetics include proparacaine, lidocaine, tetracaine, benzocaine, butamben, dibucaine, oxybuprocaine, pramoxine, proxymetacaine.

Preferred anti-allergic agents include pheniramine malleate, epinastine, emedastine, azelastin, olopatadine, ketotifen, pemirolast, nedocromil, lodoxamide, cromolyn.

Preferrred immunosupressants include ciclosporine A, tacrolimus, sirolimus.

An example of a preferred corticosteroid is dexamethasone.

In an embodiment, the invention provides for a composition consisting of a) molecular iodine and a further active ingredient such as defined above, and b) a vehicle consisting of a semifluorinated alkane and optionally a non-polar co-solvent or excipient; wherein the semifluorinated alkane is of $CF_3(CF_2)_n$—$R_m$ wherein n is an integer selected from 1 to 12, and R is linear or branched alkyl or cycloalkyl with m carbon atoms, wherein m is an integer selected from 2 to 12.

In another embodiment, the invention provides for a composition consisting of a) molecular iodine and a further active ingredient such as defined above, and b) a vehicle consisting of a semifluorinated alkane and optionally a non-polar co-solvent or excipient; wherein the semifluorinated alkane is of $CF_3(CF_2)_n$—$R_m$ wherein n is an integer selected from 2 to 12, and R is linear or branched alkyl or cycloalkyl with m carbon atoms, wherein m is an integer selected from 2 to 12.

Optionally, the composition of the present invention may also comprise one or more further excipients as an additional component. The term "excipients" as used herein refers to any pharmaceutically acceptable natural or synthetic substance that may be added to the compositions of the present invention, more specifically to the vehicle of the composition to enhance or otherwise modify its physical or chemical constitution or stability or therapeutic properties.

Compounds or composition components considered as excipients may also fall under the definition of co-solvent as defined above. In one embodiment, the excipient featured in the composition of the invention is an excipient that does not support the formation of an iodine ion or oxidized iodine species, preferably said excipient does not support the formation as of any one (or combination of) the following: iodide (I—), triiodide (I3-), iodate (IO3-), or hypoiodate (IO—).

The present composition may optionally comprise one or more excipients such as, for example, an antioxidant, a preservative, a lipid or oily excipient, a surfactant or a lubricant or a combination of at least 2 excipients thereof.

Lipid or oily excipients for use in the composition of the present invention may include, for example, triglyceride oils (i.e. soybean oil, olive oil, sesame oil, cotton seed oil, castor oil, sweet almond oil), triglycerides, mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye or skin. Said lipid or oily excipient may also function as a co-solvent for molecular iodine in accordance with the purpose of a co-solvent, such as defined above.

In one embodiment, the amount of excipient featured in a composition according to the invention may be in an amount of no more than 30% (w/w), 25% (w/w), 15% (w/w) or 10% (w/w), or 5% (w/w) 2% (w/w), or about 1.0% (w/w) in respect to the total weight amount of the vehicle.

Preferably, the compositions of the invention are substantially free of water. As understood herein, the term 'substantially free', or alternatively 'essentially free' in reference to a composition constituent refers to the presence of said constituent in no more than trace amounts and that if present in trace amounts the constituent does not provide any technical contributions to the composition.

In a preferred embodiment of the invention, the compositions are essentially free of water.

In another further preferred embodiment, the compositions according to the present invention may be substantially free of a preservative, such as an antimicrobial preservative and/or a surfactant. Preferably, the compositions are free of, i.e. do not contain water and/or any one of a preservative, such as an antimicrobial preservative, or a surfactant.

Optionally, the compositions according to the present invention may be substantially free of a polymer or complexing agent which may form complexes or bind with molecular iodine, such as polyvinylpyrrolidone (PVP) or a cadexomer.

In another preferred embodiment, the compositions according to the invention may be substantially free of an iodine ion or oxidized iodine species, preferably as selected from any one (or combination of) the following: iodide ($I^-$), triiodide ($I_3^-$), iodate ($IO_3^-$), or hypoiodate ($IO^-$). Said species may include any suitable counterion or protic form there of, for example iodide may have a counterion of potassium or sodium (i.e. NaI or KI).

In a preferred embodiment, the compositions of the present invention, preferably compositions that are substantially free of water and/or compositions that are substantially free of an iodine ion or oxidized iodine species, preferably as selected from any one (or combination of) the following: iodide (I—), triiodide (I3-), iodate (IO3-), or hypoiodate (IO—), are non-staining, preferably when administered or coming into contact to any one of the following surfaces: skin or dermal tissue, eye or eye tissue, and optionally, fabric. As defined herein, the term non-staining refers to the absence of any persisting discolouration or persisting coloured residue on the site or surface to which the composition is topically applied or is coming into contact with. It has been observed that when a composition of the invention comprising molecular iodine and a semifluorinated alkane as the vehicle is initially administered to a site of topical application, such as skin or filter paper surface, some colour may be observed initially on said surface, i.e. immediately post administration, however the colouration does not persist under ambient or skin surface conditions, and no long-term discolouration or residue is observed.

Preferably, any staining or colour which is present on application of the composition of the present invention disappears or dissipates within less than 10 minutes, less than 5 minutes, or preferably less than 1 minute. Accordingly, also no color is transferred to any surface that comes into contact with the site of administration afterwards. Thus, no color is transferred, for example, to a fabric that comes into contact with the site of iodine administration, representing a major advantage over conventional, water-based antiseptic or disinfectant iodine formulations.

Without wishing to be bound by theory, it is assumed by the inventors that the lack of staining or discolouration observed in topical application of compositions according to the present invention are due to the absence of, and lack of formation of species such as iodine ion and/or oxidized iodine species such as triiodide ($I_3^-$) in the composition. The reddish-brown or yellow colour of many aqueous-based iodine formulations and corresponding discolouration and staining of skin and other surfaces are generally attributed to such species, in particular to triiodide. As discolouration to the skin or cross-contamination to clothing may be avoided or reduced, the compositions of the invention may be advantageous in terms of improving patient compliance, where the compostion is used as a medicament In another, and optional aspect, the compositions of the invention may alternatively be formulated so as to provide a staining effect; the composition may comprise at least one component species (i.e. triiodide ($I_3^-$)), excipient or co-solvent which is coloured or staining, or which results in a composition that is staining. Preferably, said compositions are adapted for use in applications where staining or colouration may be useful as an indicator of the surface area to which the composition has been applied or contacted to, for example, in an application such as surgery. Examples of staining compositions are those comprising a semifluorinated alkane and an alcohol co-solvent.

It has also been found that the compositions of the present invention appear to be highly stable, surprisingly even when formulated at relatively higher as well as at lower concentrations of molecular iodine. State of the art compositions, such as provided for ophthalmic application are typically based on aqueous formulations comprising 5 w/v % povidone-iodine complex (e.g. Minims®, Betadine®), which provide only 0.5% available iodine, with ultimately only around 2.5 ppm (parts per million) molecular iodine as the active species.

As will be described in further detail below in the Examples, the compositions of the invention comprising a vehicle consisting of semifluorinated alkane and/or a perfluorocarbon do not undergo any physical change, such as precipitation of molecular iodine, the formation of solid or particulate species or aggregates out of solution, after prolonged period of storage, and formulations at higher concentrations of the active molecular iodine may be formulated. Compositions based on liquid or solid vehicles of one or a mixture of semifluorinated alkane and co-solvents or excipients, which do not lead to the formation of species which lead to staining, such as hydrocarbon compounds, are also observed to be stable and non-staining, and also permit the formulation of high concentrations of molecular iodine (i.e. more than 100, 250, 500 ppm or up to 1000 ppm molecular iodine).

In the context of therapeutic applications relying on topical administration to a tissue surface of a patient or subject, preferably a human patient, it is important that compositions may be readily and consistently be applied and distributed over said surface. For example, where the tissue surface is the skin, or the surface tissues of the eye, a composition needs also to reach out e.g. to folds/crevices formed by the tissue, which have limited direct accessibility. The molecular iodine compositions formulated with a vehicle based on a semifluorinated alkane according to the invention provide compositions with good spreadability for topical application. Achieving patient-friendly compositions which have positive sensory attributes is also advantageous, for instance in terms of achieving patient compliance. The semifluorinated alkane compositions according to the invention provide a pleasant and 'silky' sensation when applied, for example to the eye or the skin.

In a preferred embodiment, the composition of the present invention, is stable at for at least 30 days, preferably at room temperature. In further embodiments, the composition is preferably stable for at least 90 days, more preferably stable for at least 180 days at room temperature.

In a further preferred embodiment, the composition of the present invention, is stable without protection from light; preferably the composition is stable for at least 30 days; more preferably, stable for at least 90 days; or even more preferably, stable for at least 180 days at room temperature without protection from light.

Composition stability may be determined by comparison of properties to that observed for the composition when first prepared. Properties which may be used to determine stability include the determination of molecular iodine content by analytical methods known in the art for determining molecular iodine content (such as uv-vis measurements), or the presence of other iodine species (e.g. staining tests, uv-vis measurements). Stability may also be assessed by comparing overall visual appearance of the composition for physical changes such as precipitation, formation of particles and changes in colouration.

The iodine compositions of the invention are stable within a broad range of concentrations of molecular iodine, without requiring the inclusion of many additional excipients and composition components. For example, the compositions of the present invention may be prepared without the use of additional stabilizing agents such as buffering or pH-adjusting agents, or complexing agents to enhance solubility of iodine which may be typically required for aqueous based compositions comprising iodine.

In another aspect of the present invention, the composition may be formulated as any one of a solution, semi-solid, cream, lotion, ointment, or as a swab.

The compositions in accordance with the present invention such as described in any one of the above embodiments may also be used in therapy, as a medicine or medicament.

In a particular embodiment, the compositions may be used as an antiseptic and/or as a disinfectant in the treatment or prevention of a disease or condition in a subject in need thereof. Preferably, the compostions of the invention may be used to prevent or inhibit, the growth or proliferation of a microorganism.

As used herein, the term 'antiseptic' refers to a composition which prevents or inhibits the growth of microorganisms and/or may destroy microorganisms, in particular those which may cause infection or sepsis, and may be synonymous with the terms anti-microbial or biocide. The term 'disinfectant' refers to to a composition which inhibit or prevent proliferation of a microorganisms and/or destroy microorganisms that is topically applied to a subject, but more preferably to an inanimate surface to which a subject will or may have contact.

As understood herein, the use of a composition of the present invention in the context of prevention of a disease or condition, or in a prophylactic treatment refers to use of said composition so as to prevent occurrence, or exarcerbation, or risk of occurrence said disease or condition in a subject. For example, a subject who has a minor cut or surface wound on their skin may use and topically apply the composition to said minor cut or surface wound to the skin to destroy and/or inhibit the growth and proliferation of any microorganism, in order to avoid infection and allow for quicker healing thereof.

The composition according to any of the above embodiments may, in particular, be used for use treatment or prevention of a disease or condition affecting the skin, or mucosal tissue, wherein the composition is topically administered to the skin and/or mucosal tissue. As understood herein, the term 'skin' refers to dermal tissue, including the various layers, associated tissues or cellular layers, i.e. the epidermis (i.e. stratum corneum and vital, or living epidermis), the dermis or derma and hypodermis, and in all its forms. The composition may be administered to the skin on any surface of a subject. Preferably, it is administered to the skin which is injured or non-intact, such as to a cut, laceration, abrasion, burn, or a wound.

Mucosal tissue refers to tissue comprising epithelial cells and connective tissue and may preferably be mucosal tissue or membrane of the nose, mouth or buccal cavity.

In a further aspect, the composition according to any of the above embodiments may, also be used for the treatment or prevention of a disease or condition affecting the eye or an ophthalmic tissue, wherein the composition is topically administered to the eye or ophthalmic tissue. Ophthalmic tissue refers to any anatomical aspect of the eye apparatus, for example the cornea, or conjunctiva, or meibomian glands, or the eye lid margins, or eyelashes.

In a preferred embodiment, the compostions may be topically administered to the surface of the eye and to any such region or tissue of the eye that may be accessible to topical administration, such as to the cornea or conjunctiva, or to the eyelid margins or corners.

Preferably, the compositions are used to treat or prevent a disease or condition that is associated with, or caused by a microorganism. Preferably said microorganism is pathogenic, i.e. may cause a disease. The microorganism may be selected from any one or combination of bacteria, demodex, fungi and virus. Further microorganisms for which the present compositions may be optionally therapeutically useful may be amoeba, or yeast.

Bacteria may include gram-positive or gram-negative species. In a preferred embodiment, the compositions of the invention may be used to treat or prevent diseases or conditions associated or caused by bacteria, preferably selected from any one or combination of bacteria from the genus *streptococcus, staphylococcus, enterococcus, peptostreptococcus, pseudomonas*, mycobacteria, haemophilius, *clostridium, corynebacterium, escherichia*, and *klebsiella*.

Viruses may include herpes simplex virus (HSV), adenovirus, herpes zoster virus varicella-zoster virus (VZV), picornavirus, poxvirus, influenza virus and human immunodeficiency virus (HIV).

In one preferred embodiment, the disease or condition is associated or caused by a microorganism selected from any one or combination of the group consisting of *Staphylococcus aureus, Pseudomonas aeruginosa, Candida albicans, Aspergillus brasiliensis, Streptococcus pneumoniae, Proteus mirabilis*, and *Propionibacterium acnes*.

Where the composition is for use in the treatment or prevention of a disease or condition of the eye or an ophthalmic tissue, the disease or condition to be treated is preferably selected from the group consisting of blepharitis, bacterial conjunctivitis, ocular dryness, follicular conjunctivitis, giant papillary conjunctivitis, corneal ulcer, keratitis, conjunctival neoplasia, HSV keratitis, eye allergy, neonatal conjunctivitis, ulcerative infectious keratitis, epithelial keratitis, stromal keratitis and keratoconjunctivitis epidemica.

In a particularly preferred embodiment, the compositions for ophthalmic use are formulated wherein the amount of molecular iodine in the composition is preferably less than 0.5% (w/v), less than 0.1% (w/v), less than 0.01% (w/v) or less than 0.001% (w/v).

Where the composition is for use in the treatment or prevention of a disease or condition of the skin or mucosal tissue, it is preferred that the composition may be used to treat non-intact skin or mucosal tissue, preferably selected from a wound, a cut, a surgical wound, burn, abrasion, laceration, ulcer, rash, and sore. In another embodiment, the composition may be used to prevent infection or microorganism proliferation in a site where skin or mucosal tissue is not intact, preferably at a site of a wound, a cut, a surgical wound, a burn, an abrasion, a laceration, an ulcer, a rash, or a sore. In further embodiment, the composition of the present invention may be used to treat or prevent a disease or condition, preferably as acne, or an infection, preferably a fungal and/or bacterial infection, for example, athletes foot.

In particular preferred embodiments, the compositions for use in the treatment of a disease or condition of the skin or mucosal tissue are formulated wherein the amount of molecular iodine in the composition is preferably at least 0.01% (w/v), at least 0.1% (w/v), at least 0.5% (w/v).

In a further embodiment of the invention, the compositions for therapeutic or prophylactic use may be topically administered to a tissue or organ, at any one or more instances of prior to, during, or subsequent to a surgical or medical procedure. In a preferred embodiment, the compositions may be topically administered prior to surgery, i.e pre-operatively to a tissue or organ prior to surgical procedure on said tissue or organ; for example prior to, during, or subsequent to a cataract surgery, LASIK surgery, corneal abrasion or intravitreal injection (to prevent bacteria present on the cornea or conjunctiva from being carried over into the interior of the eye).

The use of a composition as described in any one of the above embodiments, in the manufacture or preparation of a medicament or a medicine for the treatment or prophylactic treatment of a subject in need thereof in relation to any one of diseases or conditions as described herein are also provided for in the context of the present invention.

Further provided for within the context of the present invention, are also methods of treating or prophylactically treating a subject with, or likely to be afflicted with, any one of the diseases or conditions as described herein, wherein the methods may comprise the topical administration of any one of the defined compositions to said subject. For instance, where the composition is administered to the eye, the composition may be directly topically instilled to the eye or an ophthalmic tissue.

Said treatment methods and compositions for therapeutic use are moreover preferably targeted towards human subjects, but also to veterinary subjects, such as mammals, such as canines, felines, horses, or other livestock.

In another aspect, the present invention may relate to the use of a composition according to any of the above embodiments, in a cosmetic preparation.

In yet another aspect, the composition according to any of the above embodiments may also be used as a disinfectant or an antiseptic, wherein the composition is administered to an animate and/or an inanimate surface. In one preferred embodiment, the composition may be used as a disinfectant for an inanimate surface, preferably a surface of a surgical tool, instrument or means.

Moreover, the invention may also provide to a kit comprising a composition according to the invention as described herein, wherein the kit comprises a container adapted for holding and/or storing the composition and a dispenser adapted for topical administration of the composition to a subject or a surface in need thereof.

The present invention may include the following numbered items:
1. A composition comprising molecular iodine and a vehicle comprising a semifluorinated alkane and/or a perfluorocarbon.
2. A composition according to item 1, wherein the composition is substantially free of water.
3. A composition of any of items 1 or 2, wherein the perfluorocarbon compound is a perfluorinated hydrocarbon with 5 to 12 carbon atoms.
4. A composition of any of the preceding items, wherein the perfluorocarbon is a compound of formula $F(CF_2)_nF$, wherein n is an integer selected from 5 to 12.
5. A composition of any of the preceding items, wherein the perfluorocarbon is selected from perfluorooctane, or perfluorodecalin, and perfluorooctyl bromide.
6. The composition of any one of the preceding items wherein the semifluorinated alkane is of formula (I):

$$CF_3(CF_2)_n-R_m \qquad \text{Formula (I)}$$

wherein n is an integer selected from 1 to 12, and R is linear or branched alkyl, or a cycloalkyl with m carbon atoms, wherein m is an integer selected from 2 to 12.
7. The composition of item 6, wherein the semifluorinated alkane is of formula (II):

$$CF_3(CF_2)_n-(CH_2)_mCH_3 \qquad \text{Formula (II)}$$

wherein n and m are each independently selected from an integer from 3 to 10.
8. The composition according item 7, wherein the semifluorinated alkane is selected from F4H5, F4H6, F4H8, F6H6, F6H8, F8H8 and F10H5, preferably selected from F4H5, and F6H8.
9. The composition according to any one of the preceding items, wherein the molecular iodine is dissolved in the vehicle.
10. The composition according to any one of the preceding items, wherein the amount of molecular iodine dissolved in the vehicle is less than 1 mg/mL, 0.8 mg/mL, 0.6 mg/mL, 0.5 mg/mL, 0.2 mg/mL, 0.1 mg/mL, 0.05 mg/mL, 0.02 mg/mL, 0.01 mg/mL, or less than 0.001 mg/mL.
11. The composition according to any one of the preceding items, wherein the composition is free of an iodine species from the group consisting of any one or combination of an iodide ($I^-$), triiodide ($I_3^-$), iodate ($IO_3^-$), or hypoiodate ($IO^-$).
12. The composition according to any one of the preceding items, wherein the composition further comprises an active ingredient dissolved in the vehicle, optionally selected from the group consisting of antibiotics, anti-inflammatory agents, analgesics, anaesthetics, immunosuppressants, and anti-allergic agents.
13. The composition according to any one of the preceding items, wherein the vehicle further comprises a co-solvent, preferably selected from an alcohol, or non-polar solvent or from a mixture thereof.
14. The composition according to any one of the preceding items, wherein the co-solvent is a solvent that does not support the formation of an iodine ion or oxidized iodine species, preferably wherein the co-solvent is a solvent that does not support the formation of any one or combination of iodide (I—), triiodide (I3-), iodate (IO3-), or hypoiodate (IO—).
15. The composition according to item 13 or 14, wherein the co-solvent is a non-polar solvent selected from any one or mixture of a saturated hydrocarbon or alkane, such as pentane, hexane, heptane, or octane; mineral oil, paraffin, and a siloxane.
16. The composition according to item 13 or 14, wherein the co-solvent is an alcohol selected from any one or mixture of ethanol, methanol or isopropanol, preferably absolute ethanol, methanol or isopropanol.
17. The composition according to any one of the items 13 to 16, wherein the vehicle comprises said co-solvent in an amount of up to about 38 wt % relative to the total weight of the vehicle.
18. The composition according to any one of the preceding items, wherein the vehicle consists of a semifluorinated alkane and/or a perfluorcarbon.
19. The composition according to any one of the preceding items, wherein the amount of molecular iodine dissolved in the composition or vehicle is at least 1 mg/mL, or up to 20 mg/mL.
20. The composition according to any one of the preceding items, wherein the composition comprises molecular iodine and a vehicle consisting of at least one semifluorinated alkane and/or a perfluorocarbon.
21. The composition according to any one of the preceding items, wherein the composition consists of molecular iodine and the vehicle, wherein the vehicle consists of a semifluorinated alkane and/or a perfluorocarbon, and optionally, an active ingredient, and further optionally, a co-solvent, such as ethanol, or an excipient.
22. The composition according to any one of the preceding items, wherein the composition consists of molecular iodine and a vehicle consisting of a semifluorinated alkane and/or a perfluorocarbon.
23. The composition according to any one of the preceding items, wherein the composition is non-staining when applied to a surface or tissue; preferably any one of skin, mucosal tissue, eye or eye tissue, or fabric.
24. The composition according to any one of the preceding items, wherein the composition is stable for at least 30 day, preferably stable for at least 90 days, more preferably stable for at least 180 days, optionally the composition is stable without protection from light.
25. The composition according to item 24, wherein the composition is stable at room temperature (15-25° C.).
26. The composition according to any one of the preceding claims, wherein the composition is formulated as a liquid, semi-solid, cream, lotion, ointment, or a swab.
27. The composition according to any one of the preceding items, for use as a medicine.
28. The composition according to any one of the preceding items, for use as an antiseptic and/or a disinfectant.
29. The composition according to item 27 to 28 for use in the treatment or prevention of a disease or condition affecting the skin or mucosal tissue, wherein the composition is topically administered to said organ or tissue.
30. The composition according to any one of items 27 to 29 for use in the treatment or prevention of a disease or condition affecting the eye or an ophthalmic tissue, wherein the composition is topically administered to the eye or ophthalmic tissue.
31. The composition for use according to any one of items 27 to 30, wherein the disease or condition is associated with, or caused by a microorganism.
32. The composition for use according to item 31, wherein the microorganism selected from any one or combination of bacteria, demodex, fungi, yeast or virus.
33. The composition for use according to any one of items 27 to 32, wherein disease or condition is associated or caused by a microorganism is selected from any one or combination of the group consisting of *Staphylococcus aureus, Pseudomonas aeruginosa, Candida albicans, Aspergillus brasiliensis, Streptococcus pneumoniae, Proteus mirabilis, Propionibacterium acnes.*
34. The composition for use according to to any one of items 27 to 33, wherein the composition is for use in the treatment or prevention of a disease or condition of the skin or mucosal tissue, preferably selected from a wound, a cut, an abrasion, a burn, a surgical site wound, an ulcer, a sore, acne, and an infection.
35. The composition for use according to items 27 to 33, wherein the composition is for use in the treatment or prevention of a disease or condition of the eye or an ophthalmic tissue, preferably selected from the group consisting of blepharitis, bacterial conjunctivitis, ocular dryness, follicular conjunctivitis, giant papillary conjunctivitis, corneal ulcer, keratitis, conjunctival neoplasia, HSV keratitis, eye allergy, ulcerative infectious keratitis, epithelial keratitis, stromal keratitis, keratoconjunctivitis epidemica, and neonatal conjunctivitis.
36. A composition for use according to any one of items 27 to 35, wherein the therapeutic use or preventative use comprises topical administration of the composition to a tissue, at any one instance or combination of prior to, during, or subsequent to a surgical or medical procedure.
37. A composition for use according to items 36, wherein the surgical or medical procedure is an ophthalmic procedure, preferably cataract surgery, LASIK, corneal abrasion, or intravitreal injection.
38. A method of treating or preventing a disease or condition associated or caused by a microorganism, preferably selected from any one or combination of bacteria, demodex, fungi, or virus, comprising topically administering a composition of any one of items 1 to 26 to a subject, preferably to the skin or muscosal tissue, or an eye or ophthalmic tissue of a subject in need thereof; preferably wherein infection or microorganism growth is inhibited or prevented, and optionally wherein the composition is administered at any one instance or combination of a) prior to, b) during, or c) subsequent to a surgical or medical procedure.
39. Use of a composition according to any one of item 1 to 26, in the manufacture of a medicament for use in the treatment of a disease or condition associated or caused by a microorganism, preferably selected from any one or combination of bacteria, demodex, fungi, or virus; preferably wherein the medicament is topically administered to a subject and/or adapted for topical administration to dermal tissue, mucosal tissue, to an eye or ophthalmic tissue of a subject.
40. Use of a composition according to any one of items 1 to 26 as a disinfectant or an antiseptic, preferably wherein the composition is administered to an animate and/or an inanimate surface.
41. The use of a composition according to any one of items 1 to 26 as a disinfectant for an inanimate surface, preferably wherein the inanimate surface is a surface of a surgical tool or means.
42. Use of a composition according to any one of items 1 to 26 in a cosmetic preparation.
43. A kit comprising a composition according to any of items 1 to 26, wherein the kit comprises a container adapted for holding and/or storing the composition and a dispenser adapted for topical administration of the composition to a subject or a surface in need thereof.
44. The composition according to any of the items 6 to 24, wherein the composition consists of up to about 1.0 mg/mL molecular iodine dissolved in a vehicle consisting of 1-perfluorohexyl-octane or 1-perfluorbutyl-pentane, optionally comprising a non-polar solvent.

45. The composition according to any of the items 6 to 24, wherein the composition consists of up to about 0.5 mg/mL molecular iodine dissolved in a vehicle comprising or consisting of perfluorohexyl-ethane, optionally comprising a non-polar solvent.

The present invention may also include the following items:

1.1 A composition comprising:
   a) molecular iodine, and
   b) a vehicle comprising a semifluorinated alkane;
   wherein the semifluorinated alkane is of formula (I):

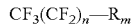  Formula (I)

wherein n is an integer selected from 1 to 12, and R is linear or branched alkyl or cycloalkyl with m carbon atoms, wherein m is an integer selected from 2 to 12.

1.2 A composition consisting of:
   a) molecular iodine and optionally, a further active ingredient, and
   b) a vehicle consisting of a semifluorinated alkane and optionally a non-polar co-solvent or excipient;
   wherein the semifluorinated alkane is of formula (I):

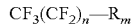  Formula (I)

wherein n is an integer selected from 1 to 12, and R is linear or branched alkyl or cycloalkyl with m carbon atoms, wherein m is an integer selected from 2 to 12.

1.3 The composition according to any one of the preceding items, wherein the molecular iodine is dissolved in the vehicle in an amount of up to about 20 mg/mL.

1.4 The composition according to any one of the preceding items, wherein the molecular iodine is dissolved in the vehicle in an amount of up to about 1 mg/mL, optionally in the range from about 0.001 mg/mL to 1 mg/mL.

1.5 The composition according to any one of the preceding items, wherein the composition comprises a further active ingredient dissolved in the vehicle, optionally selected from the group consisting of antibiotics, anti-inflammatory agents, analgesics, anaesthetics, immunosuppressants and anti-allergic agents.

1.6 The composition according to any one of the preceding items, wherein the vehicle further comprises a co-solvent, preferably an alcohol or a non-polar solvent and optionally in an amount of no more than 38% (w/w) in respect to the amount of the vehicle.

1.7 The composition according to any one of the preceding items, wherein the vehicle comprises a non-polar solvent or excipient.

1.8 The composition according to item 1.7, wherein the non-polar solvent or excipient is in an amount of no more than 38% (w/w) in respect to the amount of the vehicle, or in an amount of no more than 30% (w/w), 25% (w/w), 15% (w/w) or 10% (w/w), or 5% (w/w) 2% (w/w), or about 1.0% (w/w) in respect to the total weight amount of the vehicle.

1.9 The composition according to claim item 1.7 or 1.8, wherein the non-polar co-solvent is selected from any one or mixture of a saturated hydrocarbon; mineral oil; paraffin; siloxane; and a perfluorocarbon.

1.10 The composition according to any one of the preceding items, wherein the composition is essentially free of water.

1.11 The composition according to any one of the preceding items, wherein the composition is free of an iodine species from the group consisting of any one or combination of iodide ($I^-$), triiodide ($I_3^-$), iodate ($IO_3^-$), or hypoiodate ($IO^-$).

1.12 The composition according any one of the preceding items, wherein the composition is non-staining, optionally wherein the composition is stable at room temperature for at least 30 days, preferably stable for at least 90 days, or more preferably, stable for at least 180 days.

1.13 The composition according to any one of the preceding items, wherein the composition consists of molecular iodine and a vehicle consisting of a semifluorinated alkane.

1.14 The composition of any one of the preceding items, wherein the semifluorinated alkane is of formula (II):

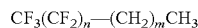  Formula (II)

wherein n and m are each independently selected from an integer from 3 to 10, optionally wherein the semifluorinated alkane is selected from $CF_3(CF_2)_3-(CH_2)_4CH_3$ (F4H5), $CF_3(CF_2)-(CH_3)_5CH_3$ (F4H6), $CF_3(CF_2)_5-(CH_2)_5CH_3$ (F6H6), $CF_3(CF_2)_5-(CH_2)_7CH_3$ (F6H8), $CF_3(CF_2)_3-(CH_2)_7CH_3$ (F4H8), $CF_3(CF_2)_7-(CH_2)_7CH_3$ (F8H8) and $CF_3(CF_2)_9-(CH_2)_4CH_3$ (F10H5), or more preferably selected from $CF_3(CF_2)_3-(CH_2)_4CH_3$ (F4H5) and $CF_3(CF_2)_5-(CH_2)_7CH_3$ (F6H8).

1.15 The composition of any one of the preceding items, wherein the semifluorinated alkane is of formula (II):

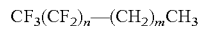  Formula (II)

wherein n is an integer selected from 2 to 9 and m is an integer from 1 to 7, optionally wherein the semifluorinated alkane is selected from $CF_3(CF_2)_3-(CH_2)_4CH_3$ (F4H5), $CF_3(CF_2)_3-(CH_2)_5CH_3$ (F4H6), $CF_3(CF_2)_5-CH_2CH_3$ (F6H2), $CF_3(CF_2)_5-(CH_2)_5CH_3$ (F6H6), $CF_3(CF_2)_5-(CH_2)_7CH_3$ (F6H8), $CF_3(CF_2)_3-(CH_2)_7CH_3$ (F4H8), $CF_3(CF_2)_7-(CH_2)_7CH_3$ (F8H8) and $CF_3(CF_2)_9-(CH_2)_4CH_3$ (F10H5).

1.16 The composition according to any one of the preceding items, wherein the composition consists of up to about 1.0 mg/mL molecular iodine dissolved in a vehicle consisting of 1-perfluorohexyl-octane or 1-perfluorbutyl-pentane, and optionally non-polar solvent.

1.17 The composition according to any one of the preceding items, wherein the composition consists of up to about 0.5 mg/mL molecular iodine dissolved in a vehicle consisting of perfluorohexyl-ethane, and optionally a non-polar solvent.

1.18 The composition according to any one of the preceding items, wherein the composition is formulated as a liquid, semi-solid, cream, lotion, ointment, or a swab.

1.19 The composition according to any one of the preceding items for use as a medicine.

1.20 The composition according to item 1.19, for use as an antiseptic and/or as a disinfectant in the treatment or prevention of a disease or condition in a subject in need thereof.

1.21 The composition according to any one of items 1.19 or 1.20, for use in the treatment or prevention of a disease or condition affecting:
   a) the skin or mucosal tissue; or
   b) the eye or an ophthalmic tissue;
   wherein the composition is topically administered to said organ or tissue.

1.22 The composition for use according to any one of items 1.20 or 1.21, wherein the disease or condition is associated with, or caused by a microorganism, preferably selected from any one or combination of bacteria, demodex, fungi, or virus.

1.23 The composition for use according to any of the items 1.19 to 1.22, wherein the composition is for use in the treatment or prevention of a disease or condition of:
  a) the eye or an ophthalmic tissue selected from the group consisting of blepharitis, bacterial conjunctivitis, ocular dryness, follicular conjunctivitis, giant papillary conjunctivitis, corneal ulcer, keratitis, conjunctival neoplasia, HSV keratitis, eye allergy, ulcerative infectious keratitis, epithelial keratitis, stromal keratitis, neonatal conjunctivitis and keratoconjunctivitis epidemica.
  b) the skin, epithelial or mucosal tissue selected from a wound, a cut, a surgical wound, burn, abrasion, laceration, ulcer, rash, sore, acne, and infection.
1.24 A composition for use according to any one of items 1.19 to 1.23, wherein the treatment or preventative use comprises topical administration of the composition to a tissue, at any one or more instances of prior to, during, or subsequent to a surgical or medical procedure.
1.25 A method of treating or preventing a disease or condition associated or caused by a microorganism, preferably selected from any one or combination of bacteria, demodex, fungi, or virus, comprising topically administering a composition of any one of items 1.1 to 1.18 to a subject, preferably to the skin or muscosal tissue, or an eye or ophthalmic tissue of a subject in need thereof; preferably wherein infection or microorganism growth is inhibited or prevented, and optionally wherein the composition is administered at any one instance or combination of a) prior to, b) during, or c) subsequent to a surgical or medical procedure.
1.26 Use of a composition according to any one of items 1.1 to 1.18, in the manufacture of a medicament for use in the treatment of a disease or condition associated or caused by a microorganism, preferably selected from any one or combination of bacteria, demodex, fungi, or virus; preferably wherein the medicament is topically administered to a subject and/or adapted for topical administration to dermal tissue, mucosal tissue, to an eye or ophthalmic tissue of a subject.
1.27 Use of a composition according to any one of items 1.1 to 1.18 as a disinfectant or an antiseptic, preferably wherein the composition is administered to an animate and/or an inanimate surface.
1.28 The use of a composition according to any one of items 1.1 to 1.18 as a disinfectant for an inanimate surface, preferably wherein the inanimate surface is a surface of a surgical tool or means.
1.29 Use of a composition according to any one of items 1.1 to 1.18 in a cosmetic preparation.
1.30 A kit comprising a composition according to any of items 1.1 to 1.18, wherein the kit comprises a container adapted for holding and/or storing the composition and a dispenser adapted for topical administration of the composition to a subject or a surface in need thereof.

The following examples serve to illustrate the invention, however should not to be understood as restricting the scope of the invention.

EXAMPLES

Example 1—Compositions (A) $I_2$ in F4H5

Molecular iodine ($I_2$) solutions in the semifluorinated alkane F4H5 at target concentrations of 0.01 mg/ml, 0.05 mg/ml, 0.1 mg/mL, 0.5 mg/mL, 0.55 mg/ml and 0.94 mg/mL were prepared. Molecular iodine was weighed into clear glass vials, followed by addition of the calculated volume of semifluorinated alkane F4H5. The compositions were stirred for 2 hours at room temperatures. The compositions provided clear pink solutions, ranging from strong pink/violet color at high concentrations (0.55 mg/ml) to very dilute pinkish colour at lower concentrations (0.01 mg/ml).

The 0.94 mg/ml solution was prepared by adding additional F4H5 to a composition comprising 1.0 mg/mL molecular iodine until all remaining molecular iodine particles were dissolved, providing a clear solution of deep pink/violet colour.

(B) $I_2$ in F6H8

Molecular iodine ($I_2$) solutions in the semifluorinated alkane F6H8 at target concentrations of 0.1 mg/mL, 0.5 mg/mL and 1.0 mg/mL were prepared. Molecular iodine was weighed into clear glass vials, followed by addition of the calculated volume of semifluorinated alkane F6H8. The compositions were stirred for 2 hours at room temperature The compositions at 0.1 mg/mL and 0.5 mg/mL concentrations provided clear pink solutions, ranging from strong pink/violet color at high concentrations (0.50 mg/ml) to dilute pink colour at lower concentration (0.1 mg/ml).

Additional F6H8 was added to the target 1.0 mg/mL composition until all remaining molecular iodine particles were dissolved, providing a clear solution, with a concentration of about 0.88 mg/mL. The solution is a deep pink/violet in colour.

(C) $I_2$ in perfluorodecalin (octadecafluorodecalin, $C_{10}F_{18}$)

A 0.2 mg/ml molecular iodine ($I_2$) solution in perfluorodecalin was prepared by weighing molecular iodine into a clear glass vial, followed by addition of the calculated volume of perfluorodecalin. The composition was stirred overnight at room temperature to provide a clear pink solution.

(D) $I_2$ in F8H8 or F10H5

A composition of 0.2 mg/ml molecular iodine ($I_2$) and F8H8 and a composition of 0.1 mg/ml of molecular iodine ($I_2$) and F10H5 were prepared, respectively, by weighing molecular iodine into a clear glass vial, followed by addition of the calculated amount of semifluorinated alkane to the vial. The molecular iodine was dissolved in the respective semifluorinated alkanes by stirring with waterbath (45° C.) heating to result in clear pink solutions. Upon cooling to room temperature, the composition prepared with F8H8 provided a pink coloured semi-solid, while the composition with F10H5 resulted in a pinkish coloured solid. On application to the skin, both compositions were observed to change to a liquid state upon contact with the skin.

(E) $I_2$ in F4H5+EtOH

Solutions with higher $I_2$ concentrations may be prepared with the addition of ethanol (non-absolute or alternatively absolute). F4H5/EtOH—Concentrations of about 20 mg/mL of $I_2$ in F4H5 are achieved when ethanol is added to an amount of 38% (w/w), relative to the weight of the vehicle The resulting compostion is a red-brown coloured solution.

F4H5/EtOH—Solutions comprising 3 mg/mL iodine were prepared by adding 1.5% (w/w) ethanol (or alternatively 1.0% (w/w)) relative to the weight of the F4H5/EtOH liquid vehicle. The compositions are brown-pink coloured clear solutions.

(F) $I_2$ in F6H8+EtOH

F6H8/EtOH—Solutions with higher $I_2$ concentrations may be prepared with the addition of ethanol (non-absolute or alternatively absolute). Concentrations of about 20 mg/mL of $I_2$ in F6H8 are achieved when ethanol is added to an amount of 38% (w/w), relative to the weight of the vehicle.

F6H8/EtOH—comprising 3 mg/ml iodine were prepared by adding 1.5% (w/w) ethanol (or alternatively 1.0% (w/w)) relative to the weight of the F6H8/EtOH liquid vehicle. The compositions are reddish-brown coloured clear solutions.

Example 2—Composition Stability

Saturated iodine solutions as prepared in Example 1 above of $I_2$ in F4H5 (0.94 mg/mL) and F6H8 (0.88 mg/mL) were stored standing under ambient atmosphere and temperature conditions under a capped clear glass vial for 52 weeks without protection from light. No visible changes in terms of colour, or appearance of particles forming either in solution, or on the glass walls were observed.

In contrast, the formation of particles in solution and on the glass walls were observed for the Iodine solutions as prepared in Example 1 above of $I_2$ in the F4H5/Ethanol or F6H8/Ethanol liquid vehicles.

The stability of compositions of iodine (12) dissolved the semifluorinated alkanes F4H5 and F6H8 at further concentrations of 0.01 mg/mL, 0.05 mg/mL, 0.1 mg/mL, 0.5 mg/mL and 0.9 mg/mL, stored in closed clear-glass crimp cap vials (minimum composition volume of 10-mL) are tested. Comparative compositions, such as with alternative vehicles such as aqueous-based and other organic compounds are also formulated and tested for comparison.

Samples of the compositions are stored at ambient conditions (room temperature), while some samples are aged or stress-condition testing, for example under UV-stress conditions (to evaluate light sensitivity) or stored at non-ambient temperatures.

The compositions are assessed at intervals over time, for example via: visual inspection of the vials to observe and record any visible changes to the compositions such as precipitation, formation of deposits, etc, as well as staining tests; measuring the content of molecular iodine (and other iodine species) e.g. by uv-vis measurements, and other analytical methods in the art for analysing iodine content.

Example 3—Antimicrobial Effectiveness (A) Ph. Eur. 5.1.3
Solutions of $I_2$ in F4H5 (0.85 mg/mL) and $I_2$ in F6H8 (0.85 mg/mL) were tested for their efficacy of antimicrobial preservation according to current edition Ph. Eur. 5.1.3. under the acceptance criterium for parenteral preparations, eye preparations, intrauterine preparations and intramammary preparations. Both solutions were found to be fully compliant within the guidelines. The tests were conducted for both formulations with the following microorganisms: *Pseudomonas aeruginosa*, *Staphylococcus aureus*, *Candida albicans*, and *Aspergillus brasiliensis*.

(B) Hemmhof Test/Agar diffusion test
Hemmhof tests, or Agar diffusion tests were performed on the following compositions:
$I_2$ (3 mg/mL) solution in F6H8 and EtOH 1.5% (w/w) as prepared in Example 1

$I_2$ (3 mg/mL) in F6H8 and EtOH 1.5% (w/w) as prepared in Example 1 Organisms tested included *Staphylococcus aureus* ATCC 6538, *Pseudomonas aeruginosa* ATCC 9027, *Streptococcus pneumoniae* ATCC 33400, *Proteus mirabilis* ATCC 14153, *Candida albicans* ATCC 10231, *Propionibacterium acnes* ATCC 11828 (Anaerobier).

Both formulations exhibited inhibition zones, demonstrating effectiveness in inhibition of growth of the organisms tested.

Example 4—Staining

Solutions of $I_2$ in F4H5 (0.85 mg/mL) and $I_2$ in F6H8 (0.85 mg/mL) were tested in respect of staining on skin. A drop of the respective compositions were administered to skin on a subject. On initial contact with the skin, the pink colour which is characteristic of the compostions was still observed, however vanished within a few seconds. No staining of the skin was observed. No color was transferred to a piece of fabric in contact with the skin afterwards.

No staining of the skin was also observed for solutions of $I_2$ at lower concentrations in F4H5 or F6H8, as well as with the compositions of molecular iodine in F8H8, F10H5 and perflurodecalin when these were topically applied to the skin.

Further staining tests are conducted on cellulose filter paper (Whatman, CAT No. 1005-070). In the tests, a drop of the respective formulations (ca. 50 µL) was added to the filter paper. The staining behaviour of the compositions were recorded afterwards.

No staining of the Whatman filter was observed for solutions of $I_2$ in F4H5, F6H8, F8H8, F10H5 and perflurodecalin.

When the same tests were conducted for the compositions of $I_2$ prepared in the F4H5/ethanol and F6H8/ethanol liquid vehicles of Example 1, staining of the Whatman filter paper was observed. Yellow-brown spots on the site of administration were left behind on the filter paper.

Example 5—Further Compositions—Stability and Staining

Further compositions of molecular iodine, in a vehicle consisting of a semifluorinated alkane and optionally a co-solvent as summarized in Table 1 below were prepared according to the methods described in Example 1, and then tested similarly to the protocols described in Examples 2 and 4 as to their stability and for staining.

Stability—Vials containing the compositions were visually inspected to determine stability. Visual inspection was performed directly after fabrication, after 1 day and after 1 week. A "Yes" in Table 1 indicates the recording of no visual changes, such as discoloration of the initial pink color of the composition, and no formation of precipitates or deposits.

Staining—Staining was assessed as detailed in Example 4 on cellulose filter paper. A "No" in Table 1 indicates that no staining effects were observed upon application of a sample of the composition to the cellulose filter.

TABLE 1

| Vehicle 1 (V1) | Vehicle 2 (V2) | Ratio V1:V2 (w/w) | Ratio V1:V2 (v/v) | $I_2$ (mg/mL) | $I_2$ (ppm) | Stability | Staining |
|---|---|---|---|---|---|---|---|
| F6H2 | — | — | — | 0.01 | 10 | yes | no |
| F6H2 | — | — | — | 0.05 | 50 | yes | no |
| F6H2 | — | — | — | 0.10 | 100 | yes | no |
| F6H2 | — | — | — | 0.25 | 250 | yes | no |

TABLE 1-continued

| Vehicle 1 (V1) | Vehicle 2 (V2) | Ratio V1:V2 (w/w) | Ratio V1:V2 (v/v) | I₂ (mg/mL) | I₂ (ppm) | Stability | Staining |
|---|---|---|---|---|---|---|---|
| F6H2 | — | — | — | 0.50 | 500 | yes | no |
| F4H5 | — | — | — | 0.01 | 10 | yes | no |
| F4H5 | — | — | — | 0.05 | 50 | yes | no |
| F4H5 | — | — | — | 0.10 | 100 | yes | no |
| F4H5 | — | — | — | 0.25 | 250 | yes | no |
| F4H5 | — | — | — | 0.50 | 500 | yes | no |
| F4H5 | — | — | — | 1.00 | 1000 | yes | no |
| F6H8 | — | — | — | 0.01 | 10 | yes | no |
| F6H8 | — | — | — | 0.05 | 50 | yes | no |
| F6H8 | — | — | — | 0.10 | 100 | yes | no |
| F6H8 | — | — | — | 0.25 | 250 | yes | no |
| F6H8 | — | — | — | 0.50 | 500 | yes | no |
| F6H8 | — | — | — | 1.00 | 1000 | yes | no |
| F8H8 | — | — | — | 0.10 | 100 | yes | no |
| Perfluorooctane | — | — | — | 0.10 | 100 | yes | no |
| F6H8 | paraffin wax | 4:1 | 4:1 | 0.20 | 200 | yes | no |
| F6H2 | F4H5 | 1.17:1 | 1:1 | 0.25 | 250 | yes | no |
| F6H2 | F6H8 | 1.12:1 | 1:1 | 0.125 | 125 | yes | no |
| F4H5 | F6H8 | 0.96:1 | 1:1 | 0.125 | 125 | yes | no |
| F6H8 | Decamethylcyclopentasiloxan | 1.41:1 | 4:1 | 0.20 | 200 | yes | no |
| 2-perfluorohexyl-octane | — | — | — | 0.50 | 500 | yes | no |
| F6H8 | Squalane | 8.33:1 | 5:1 | 0.208 | 208 | yes | no |
| F4H5:F6H8 (1:1) | Squalane | 8.15:1 | 5:1 | 0.227 | 227 | yes | no |
| F6H8 | paraffinum perliquidum | 6.67:1 | 4:1 | 0.80 | 800 | yes | no |
| F4H5 | paraffinum perliquidum | 6.37:1 | 4:1 | 0.80 | 800 | yes | no |
| F6H8 | mineral oil | 6.67:1 | 4:1 | 0.80 | 800 | yes | no |
| F4H5 | mineral oil | 6.37:1 | 4:1 | 0.80 | 800 | yes | no |
| F6H8 | octane | 7.71:1 | 4:1 | 0.80 | 800 | yes | no |
| F4H5 | octane | 7.37:1 | 4:1 | 0.80 | 800 | yes | no |

The composition of molecular iodine in a vehicle based on 4:1 ratio of F6H8 and paraffin wax was a solid formulation.

A composition comprising a semifluorinated alkane, molecular iodine and an exemplary active ingredient, cyclosporine, was also prepared. The same tests as conducted for compositions of Table 1 was conducted. The composition was also found to be stable and non-staining.

TABLE 2

| Vehicle 1 (V1) | Vehicle 2 (V2) | Ratio V1:V2 (w/w) | Ratio Vi:V2 (v/v) | API (mg/mL) | I₂ (mg/mL) | I₂ (ppm) | Stability | Staining |
|---|---|---|---|---|---|---|---|---|
| F6H8 | F4H5 | 10.5:1 | 10:1 | cyclosporine (0.091) | 0.27 | 227 | yes | no |

Example 6—EpiOcular Eye Irritation Test

The following compositions were evaluated in terms of risk for eye irritation. A model of ocular irritation, the EpiOcular Eye Irritation Test (OCL-200-EIT; MaTek Corporation), was used. The EpiOcular protocol is approved as a new OECTD Test Guideline No. 492 (Reconstructed human Cornea-like Epithelium (RhCE) test method for identifying chemicals not requiring classification and labelling for eye irritation or serious eye damage).

The following compositions were evaluated:

(a) 1.0 mg/ml iodine (1000 ppm) in 1-perfluorobutyl-pentane (F4H5)

(b) 1.0 mg/ml iodine (1000 ppm) in 1-perfluorohexyl-octane (F6H8)

(c) 0.5 mg/ml iodine (500 ppm) in 1-perfluorohexyl-ethane (F6H2).

A test material-treated tissue viability of higher than 60% relative to the negative control-treated tissue is classified as a non-irritant; a test material-treated tissue viability below 60% is considered as an irritant.

These compositions, which have relatively high concentrations of iodine, were unexpectedly found to be non-irritating. Iodine ophthalmic products in the art based on povidone-iodine complex aqueous formulations typically provide significantly lower concentrations of molecular iodine, for example about 2.5 ppm. All of the tested compositions of molecular iodine in semifluorinated alkane were classified based on this model as as non-irritating, with results of (a) 95.4%, (b) 98.4% and (c) 107.8% tissue viability respectively.

Example 7—Ex Vivo Eye Irritation Test (EVEIT)

A comparison in respect of corneal healing process was conducted for a composition comprising molecular iodine (0.25 mg/ml; 250 ppm) in 1-perfluorohexyl-octane (Composition B) with vehicle 1-perfluorohexyl-octane (Composition A) and hyaluronic acid (HYLO-COMOD®) as a reference and 0.01% BAC (benzalkonium chloride) as a control using an Ex Vivo Eye Irritation Test (EVEIT), similar to as described in M. Frentz et al, Altern. to Lab. Anim., 2008 (36) p 25-32; and N. Schrage et al, Graefes Arch Clin Exp Ophthalmol 2012 (250), 1330-1340).

Method. Rabbit corneas were obtained and placed in an artificial anterior ocular chamber which was gently filled with serum-free minimal essential medium (Eagle's MEM) containing Earle's salts and HEPES buffer for nutrition. The medium was contstantly replenished by a micropump to imitate the physiological condition of the eye. The culture chambers were held at 32° C. under normal air without supplementary CO2 and >95% relative humidity. Five corneas per test substance (n=5) were used except for the postive control with which two corneas (n=2) were tested.

After 12 h of stabilization in the culture chamber, the corneas were evaluated by microscopy and corneas with intact epithelium and without opacities were selected.

Four small abrasions (2.3-4.3 mm2) were applied to the surface of the selected corneas with a cornea drill. All defects were monitored by fluorescein sodium staining (0.17% aq. solution) and microscopy.

The test substances were administered one hour after induction of the corneal erosion and were applied six times daily onto the apex of the corneas (30-50 µL every four hours). A soft-tipped cannula, with continuous suction was placed on the lowest part of the corneoscleral region within the culturing chamber to remove any excess fluid. Experiments were terminated after 3 days of application. Biomicroscopic images of the corneas were taken daily to document the corneal healing process using a phase-contrast microscope integrated camera (KY-F1030U, JVC, (Bad Vilbel, Del.) mounted on a Z16 APO Microscope (Wetzlar, Del.)). All defects were monitored by fluorescein sodium stains (0.17% aq. solution) with yellow green fluorescence indicating the areas of epithelial defects. Erosion sizes were determined using a software tool of the microscope (DISKUS). At the end of the 3 days, the experiment was terminated and all corneas were fixed in 3.7% formaldehyde and stained with a hematoxylin-eosin dye for microscopic evaluation. To monitor the metabolic activity of the cornea, glucose and lactate concentrations were photometrically quantified in the outflow medium from the artificial anterior chambers.

Results.

The composition comprising molecular iodine in F6H8 (Composition B) did not harm the corneal healing process after the induction of corneal erosion. Instead, a similar positive outcome in respect of corneal healing was observed with Composition A (F6H8 alone) or with the standard reference hyaluronic acid composition (HYLO-COMOD®).

TABLE 3

Corneal Erosion Size Measurements/Mean mm² (SD)

| Composition | Day 0 | Day 1 | Day 2 | Day 3 |
| --- | --- | --- | --- | --- |
| A (n = 5); F6H8 | 11.29 (1.02) | 3.51 (0.69) | 0 (0) | 0 (0) |
| B (n = 5); molecular iodine in F6H8 | 12.09 (0.86) | 3.37 (1.17) | 0 (0) | 0 (0) |
| 0.01% BAC | 12.91 (0.32) | 7.42 (0.03) | 26.40 (2.18) | 42.08 (0.43) |
| HYLO COMOD ® | 12.12 (0.51) | 3.59 (1.07) | 0 (0) | 0 (0) |

No significant differences in terms of an effect of positive corneal healing was noted between composition A and composition B (comprising 250 ppm molecular iodine) With both compositions, as with the reference composition (HYLO COMOD®), the mechanically induced epithelial erosions were found to be significantly reduced and essentially absent after day 2 of treatment. Furthermore, no corneal toxicity, based on the metabolic activity as indicated by the glucose/lactate measurements was observed for these compositions. In significant contrast, the control comprising 0.01% of the preservative BAC, a progressive increase of the induced epithelial lesions was observed over the course of the three days of the experiment.

Example 7—Antimicrobial Effectiveness Test (F6H2)

Formulations of molecular iodine dissolved in the semifluorinated alkane F6H2 (0.01, 0.05, 0.1, 0.25 and 0.5 mg/ml) were tested for antimicrobial effectiveness.

Staphylococcus aureus ($10^7$ cells) were plated onto an inert plate. After a short drying time, 100 µl of the formulations of molecular iodine dissolved in perfluorohexyl-ethane (F6H2) were applied to the germs on the plate. After a specified contact time, the remaining Staphylococcus aureus cells were collected by shaking out with medium and transferred and plated to an agar plate. After incubation at 37° C. overnight, the Staphylococcus aureus cell counts were determined.

It was observed, within a contact time of 30 seconds of the Staphylococcus aureus cells on the plate, that all of the tested iodine formulations (0.01, 0.05, 0.1, 0.25 and 0.5 mg/ml) in F6H2 lead to a complete killing of all germs. No viable cell counts were observed after the incubation step overnight.

The invention claimed is:

1. A composition consisting of:
   a) molecular iodine, and
   b) a vehicle;
   wherein the vehicle consists of a semifluorinated alkane, and wherein the semifluorinated alkane is of the formula (I):

$$CF_3(CF_2)_n-R_m \qquad \text{Formula (I)}$$

wherein n is an integer selected from 1 to 12, and R is a linear or branched alkyl or cycloalkyl with m carbon atoms, wherein m is an integer selected from 2 to 12.

2. The composition according to claim 1, wherein the molecular iodine is dissolved in the vehicle in an amount of up to about 1 mg/mL.

3. The composition according to claim 1, wherein the composition is free of an iodine species selected from the group consisting of iodide (I⁻), triiodide (I₃⁻), iodate (IO₃⁻), hypoiodate (IO⁻), and any combination thereof.

4. The composition according to claim 1, wherein the composition is non-staining and stable at room temperature for at least 30 days.

5. The composition of claim 1, wherein the semifluorinated alkane is of formula (II):

$$CF_3(CF_2)_n-(CH_2)_mCH_3 \quad \text{Formula (II)}$$

wherein n and m are each independently selected from an integer from 3 to 10.

6. The composition according to claim 5, wherein the semifluorinated alkane is selected from the group consisting of CF₃(CF₂)₃—(CH₂)₄CH₃ (F4H5), CF₃(CF₂)₃—(CH₂)₅CH₃ (F4H6), CF₃(CF₂)₅—(CH₂)₅CH₃ (F6H6), CF₃(CF₂)₅—(CH₂)₇CH₃ (F6H8), CF₃(CF₂)₃—(CH₂)₇CH₃ (F4H8), CF₃(CF₂)₇—(CH₂)₇CH₃ (F8H8), and CF₃(CF₂)₉—(CH₂)₄CH₃ (F10H5).

7. The composition according to claim 5, wherein the semifluorinated alkane is selected from CF₃(CF₂)₃—(CH₂)₄CH₃ (F4H5) or CF₃(CF₂)₅—(CH₂)₇CH₃ (F6H8).

8. The composition according to claim 1, wherein the composition is formulated as a liquid or as a semi-solid.

9. The composition according to claim 1, wherein the composition consists of the molecular iodine dissolved in F4H5, F6H2 or F6H8 or a mixture thereof.

10. A kit comprising a composition according to claim 1, wherein the kit comprises a container adapted for holding and/or storing the composition, and a dispenser adapted for topical administration of the composition to a subject or a surface in need thereof.

11. The composition according to claim 1, wherein the semifluorinated alkane is of the formula (II):

$$CF_3(CF_2)_n-(CH_2)_mCH_3 \quad \text{Formula (II)}$$

wherein n is an integer selected from 2 to 9, and m is an integer selected from 1 to 7.

12. The composition according to claim 1, wherein the semifluorinated alkane is a liquid, semi-solid, or solid at room temperature.

13. The composition according to claim 1, wherein the composition consists of the molecular iodine dissolved in 1-perfluorohexyl-octane (F6H8) or 1-perfluorobutyl-pentane (F4H5).

14. The composition according to claim 1, wherein the composition consists of up to about 1.0 mg/mL of the molecular iodine dissolved in a vehicle consisting of 1-perfluorohexyl-octane (F6H8) or 1-perfluorobutyl-pentane (F4H5).

15. The composition according to claim 1, wherein the semifluorinated alkane is characterized by a boiling point of less than 140° C.

16. The composition according to claim 1, wherein the composition consists of the molecular iodine dissolved in 1-perfluorobutyl-pentane (F4H5) or 1-perfluorohexyl-ethane (F6H2).

17. The composition according to claim 1, wherein the composition consists of up to about 0.5 mg/ml of the molecular iodine dissolved in 1-perfluorohexyl-ethane (F6H2).

18. The composition according to claim 1, wherein the molecular iodine is present in an amount effective to inhibit or prevent the growth or proliferation of a microorganism.

19. The composition according to claim 18, wherein the microorganism is selected from bacteria, demodex, fungi, or virus.

20. The composition according to claim 1, wherein the semifluorinated alkane is F6H2.

21. A pharmaceutical composition formulated for topical application to the skin or eye consisting of molecular iodine dissolved in a semifluorinated alkane, wherein the semifluorinated alkane is of the formula (I):

$$CF_3(CF_2)_n-R_m \quad \text{Formula (I)}$$

wherein n is an integer selected from 1 to 12, and R is a linear or branched alkyl or cycloalkyl with m carbon atoms, wherein m is an integer selected from 2 to 12.

22. The composition according to claim 21, wherein the semifluorinated alkane is of formula (II):

$$CF_3(CF_2)_n-(CH_2)_mCH_3 \quad \text{Formula (II)}$$

wherein n and m are each independently selected from an integer from 3 to 10.

23. The composition according to claim 21, wherein the semifluorinated alkane is selected from the group consisting of F4H5, F6H2 and F6H8.

* * * * *